United States Patent
Boshoff et al.

(10) Patent No.: US 9,593,136 B2
(45) Date of Patent: Mar. 14, 2017

(54) COMPOUNDS FOR INHIBITING 1-DEOXY-D-XYLULOSE-5-PHOSPHATE REDUCTOISOMERASE

(75) Inventors: Helena I. Boshoff, Potomac, MD (US); Cynthia S. Dowd, Washington, DC (US); Emily R. Jackson, Springfield, VA (US); Kylene Kehn-Hall, Fredericksburg, VA (US); Richard E. Lee, Cordova, TN (US); Robin Lee, Cordova, TN (US); Geraldine San Jose, Mios (FR)

(73) Assignees: The George Washington University, Washington, DC (US); George Mason University, Fairfax, VA (US); St. Jude Children's Research Hospital, Inc., Memphis, TN (US); The United States of America, as Represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/130,384

(22) PCT Filed: Jun. 29, 2012

(86) PCT No.: PCT/US2012/044962
§ 371 (c)(1),
(2), (4) Date: Aug. 18, 2014

(87) PCT Pub. No.: WO2013/006444
PCT Pub. Date: Jan. 10, 2013

(65) Prior Publication Data
US 2014/0378418 A1 Dec. 25, 2014

Related U.S. Application Data

(60) Provisional application No. 61/503,736, filed on Jul. 1, 2011.

(51) Int. Cl.
| | |
|---|---|
| C07F 9/40 | (2006.01) |
| A61K 31/662 | (2006.01) |
| A01N 57/18 | (2006.01) |
| A61K 31/66 | (2006.01) |
| A01N 37/46 | (2006.01) |
| A61K 31/135 | (2006.01) |
| C12Q 1/533 | (2006.01) |

(52) U.S. Cl.
CPC ............ *C07F 9/4021* (2013.01); *A01N 37/46* (2013.01); *A01N 57/18* (2013.01); *A61K 31/135* (2013.01); *A61K 31/66* (2013.01); *C07F 9/4018* (2013.01); *C12Q 1/533* (2013.01); *G01N 2500/04* (2013.01)

(58) Field of Classification Search
None
See application file for complete search history.

(56) References Cited

U.S. PATENT DOCUMENTS

| | | | | |
|---|---|---|---|---|
| 4,792,560 | A | * | 12/1988 | Huang .......................... 514/311 |
| 7,638,505 | B2 | | 12/2009 | Van Calenbergh et al. |
| 2003/0206892 | A1 | | 11/2003 | Jaworski et al. |

OTHER PUBLICATIONS

Giessmann et al., Chemistry and Biodiversity, vol. 5, No. 4, pp. 643-656, Apr. 2008.*
Perruchon et al., Chem. Med. Chem., vol. 3, No. 8, pp. 1232-1241, Aug. 18, 2008.*
Ito et al. In Cancer Science 94(1), 3-8 (2003).*
"RN 502920-76-5" Database Registry Chemical Abstracts Service, Columbus, Ohio, Accession No. RN 502920-76-5, Entered STN: Apr. 14, 2003.*
International Preliminary Report issued on Jan. 7, 2014, in International Patent Application No. PCT/US2012/044962, 5 pages.
Silber et al. "AFMoC Enhances Predictivity of 3D QSAR: A Case Study with DOXP-Reductoisomerase," J. Med. Chem., 2005, vol. 48, pp. 3547-3563.

* cited by examiner

*Primary Examiner* — Alicia L Otton
(74) *Attorney, Agent, or Firm* — Blank Rome LLP

(57) ABSTRACT

In particular, the compound is effective to inhibit Dxr in *Mycobacterium tuberculosis* (Mtb). The present invention relates to compounds having general formula (I) or (II)

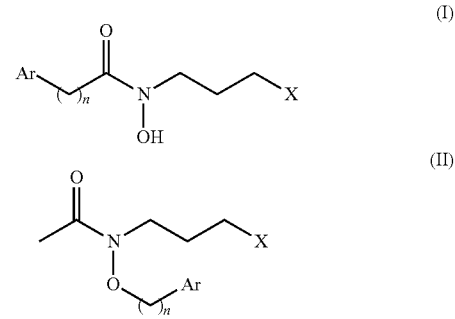

where X is an acidic group, such as carboxylate, phosphonate, sulfate, and tetrazole; Ar is a substituted or unsubstituted aromatic or heteroaromatic group; and n is 0, 1, 2, 3, or 4, preferably 2, 3, or 4. The compounds inhibits 1-deoxy-D-xylulose-5-phosphate reductoisomerase (Dxr), particularly Dxr in *Mycobacterium tuberculosis* (Mtb).

9 Claims, 2 Drawing Sheets

COMPOUNDS FOR INHIBITING 1-DEOXY-D-XYLULOSE-5-PHOSPHATE REDUCTOISOMERASE

This application is a National Phase of PCT/US2012/044962, filed Jun. 29, 2012, which claims the priority of U.S. Provisional Patent Application No. 61/503,736, filed Jul. 1, 2011, which is incorporated herein by reference.

The invention was made with government support under Grant No. IRC1A1086453 awarded by NIH. The U.S. Government has certain rights in the invention.

FIELD OF THE INVENTION

The invention relates to compounds for inhibiting 1-deoxy-D-xylulose-5-phosphate reductoisomerase (Dxr). In particular, the compound is effective to inhibit Dxr in *Mycobacterium tuberculosis* (Mtb).

BACKGROUND OF THE INVENTION

*Mycobacterium tuberculosis* (Mtb) is the causative agent of tuberculosis. Tuberculosis is primarily a disease of the lungs and is characterized by chronic coughing, blood-tinged sputum, fever, night sweats, and a loss of appetite. The current World Health Organization (WHO) approved therapy for treating TB is a four-drug combination of isoniazid, rifampicin, pyrazinamide and either ethambutol or streptomycin. This 6-month regimen for treating TB is known as directly-observed therapy short course (DOTS). New and improved drug therapies are needed that will decrease the treatment period and combat both the increasing rate of infection and the emergence of multi-drug resistant TB (MDR-TB) and extensively drug resistant TB (XDR-TB).

Two mechanisms are known for the biosynthetic production of isoprenoid units: the mevalonate pathway found in mammals and plants, and the nonmevalonate pathway found in most bacteria. There are no human homologues for the enzymes of the nonmevalonate pathway and each enzymatic reaction is vital to the survival of bacteria. These enzymes are thus prospective targets for therapeutic intervention of *M. tuberculosis*. 1-Deoxy-D-xylulose-5-phosphate reducto-isomerase (Dxr), an enzyme in the non-mevalonate pathway, is essential for the growth of Mtb. Dxr is responsible for the conversion of 1-deoxy-D-xylulose-5-phosphate (Dxp) to 2-C-methyl-D-erythritol-4-phosphate (MEP) and is the first committed step in the nonmevalonate pathway. Current anti-TB drugs do not target the nonmevalonate pathway, so Dxr inhibition would be a new mechanism of action. Accordingly, Dxr provides a convenient target for developing drugs against Mtb.

SUMMARY OF THE INVENTION

The present invention relates to compounds for inhibiting 1-Deoxy-D-xylulose-5-phosphate reducto-isomerase (Dxr). The compounds of the present invention and its derivatives have antimicrobial activities against various pathogenic microorganisms, particularly against those utilizing the non-mevalonate pathway. Accordingly, it is one object of this invention to provide compound and derivatives and salts thereof which are useful as antibiotics.

Another object of this invention is to provide methods for preparation of the compounds of the present invention and derivatives thereof.

A further object of the present invention is to provide a method for screening for compounds capable of inhibiting Dxr.

A yet further object of this invention is to provide pharmaceutical compositions comprising one or more active ingredient(s) selected from the compounds of the present invention and derivatives thereof.

The compounds of the present invention have the general formula (I) or (II)

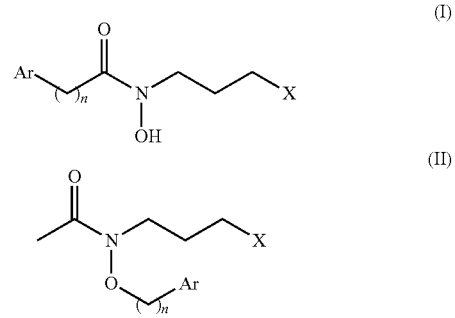

where X is an acidic group, such as carboxylate, phosphonate, sulfate, tetrazole, and esters thereof; Ar is a substituted or unsubstituted aromatic or heteroaromatic group; and n is 0, 1, 2, 3, or 4. In preferred embodiments, X is a phosphonate, esters thereof, or salts thereof. In the case of phosphonate ($-PO(OH)_2$), the resulting compounds have the structure of formula (III) or (IV)

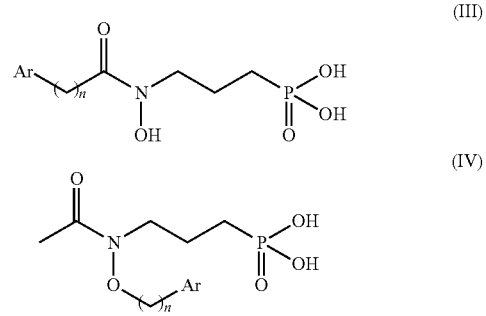

Other phosphonate esters are also contemplated by the invention.

Formulas (III) and (IV) bear structural resemblance to FR900098. However, the compounds of the present invention can bind two binding sites of Dxr, while FR900098 (or fosmidomycin) can only bind one site on Dxr. The present compounds are designed to bind to both the substrate binding site (as fosmidomycin does) and the NADP+ binding site on Dxr at the same time to provide a bridge between those binding sites. Binding to the enzyme in this way prevents both substrate and NADP+ from binding and results in efficient inhibition of the enzyme. The Ar portion of the compounds of the present invention is designed to approximate the binding of the pyridine ring found in NADP+. Substituents on the compounds are designed to mimic portions of NADP+ (such as the ribose ring, amide substituent, etc.).

Figure 2:
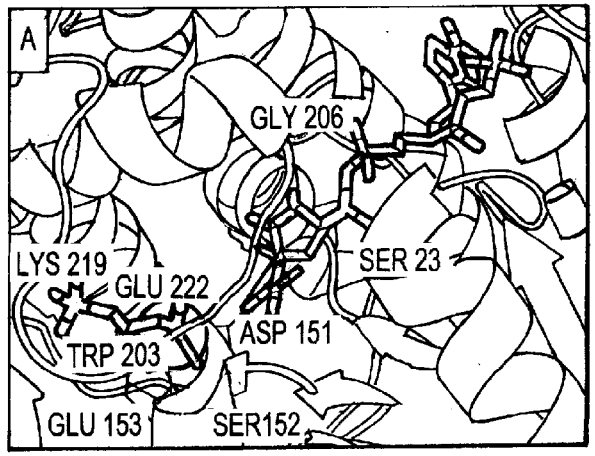
Figure 2:
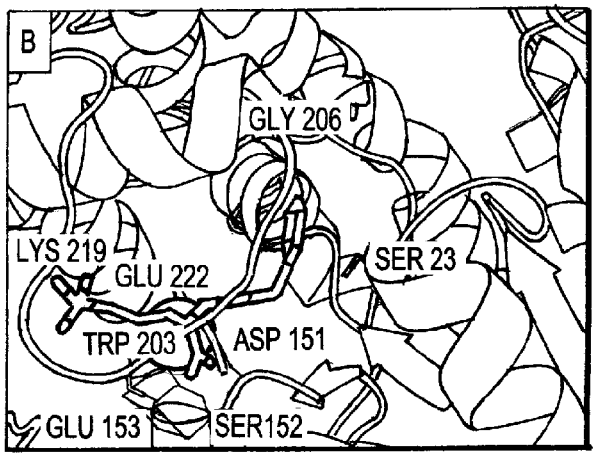
Figure 2:
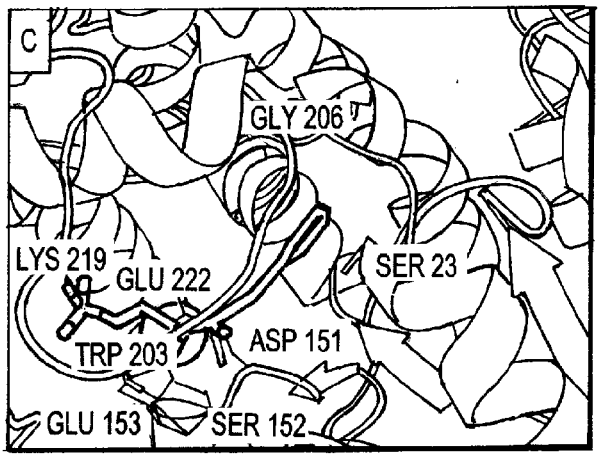

FIG. 2 is a model showing Mtb Dxr active site and docking results. (A) Active site of Mtb Dxr with the binding sites of fosmidomycin and NADPH (pdb 2jcz), (B) Docking of a representative either ligand, (C) Docking of a representative amide ligand. Protein chain A is shown as cartoon (blue), $Mn^{2+}$ as sphere (pink), ligands are shown as sticks colored by atom type, protein residues as lines colored by atom type. Hydrogen atoms have been omitted for clarity.

DETAILED DESCRIPTION OF THE PREFERRED EMBODIMENT

The present invention provides candidate compounds for the inhibition of 1-deoxy-D-xylulose-5-phosphate reductoisomerase (Dxr), preferably in *Mycobacterium tuberculosis* (Mtb). The compounds contain the general formula (I) or (II)

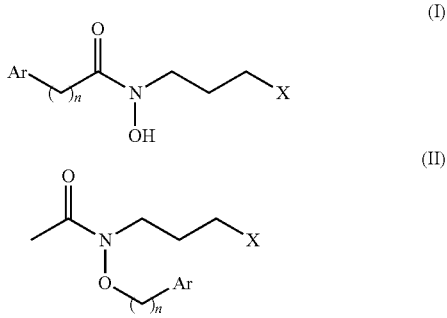

where X is an acidic group, such as carboxylate, phosphonate, sulfate, and tetrazole; Ar is a substituted or unsubstituted aromatic or heteroaromatic group; and n is 0, 1, 2, 3, or 4, preferably 2, 3, or 4.

The aromatic group can be, but is not limited to, phenyl, naphthyl, biphenyl, benzyl, anthracenyl, and phenanthracenyl. The heteroaromatic group can be, but is not limited to, pyridyl, quinolinyl, indolyl, pyrazinyl, furanyl, thiophenyl, pyrrolyl, and imidazolyl. The aromatic and heteroaromatic group can be substituted. The substitution can be, but is not limited to, alkyl, alkenyl, alkynyl, hydroxyl, alkoxy, alkoxyalkyl, cycloalkyl, thio, halo, alkylthio, aryl, heteroaryl, amino, amido, aryloxy, sulfonamido, or combinations thereof.

The term "alkyl" refers to a straight or branched hydrocarbon chain radical consisting solely of carbon and hydrogen atoms, containing solely carbon and hydrogen atoms, containing no unsaturation, having from one to eight carbon atoms, and which is attached to the rest of the molecule by a single bond, such as illustratively, methyl, ethyl, n-propyl, 1-methylethyl (isopropyl), n-butyl, n-pentyl, and 1,1-dimethylethyl (t-butyl).

The term "alkenyl" refers to an aliphatic hydrocarbon group containing a carbon-carbon double bond and which may be a straight or branched or branched chain having about 2 to about 10 carbon atoms, e.g., ethenyl, 1-propenyl, 2-propenyl (allyl), iso-propenyl, 2-methyl-1-propenyl, 1-butenyl, 2- and butenyl.

The term "alkynyl" refers to a straight or branched chain hydrocarbonyl radicals having at least one carbon-carbon triple bond, and having in the range of about 2 up to 12 carbon atoms (with radicals having in the range of about 2 up to 10 carbon atoms presently being preferred) e.g., ethynyl.

The term "alkoxy" denotes an alkyl group as defined herein attached via oxygen linkage to the rest of the molecule. Representative examples of those groups are methoxy and ethoxy.

The term "alkoxyalkyl" denotes an alkoxy group as defined herein attached via oxygen linkage to an alkyl group which is then attached to the main structure at any carbon from alkyl group that results in the creation of a stable structure at the rest of the molecule. Representative examples of those groups are $-CH_2OCH_3$, and $-CH_2OC_2H_5$.

The term "cycloalkyl" denotes a non-aromatic mono or multicyclic ring system of about 3 to 12 carbon atoms such as cyclopropyl, cyclobutyl, cyclopentyl, cyclohexyl and examples of multicyclic cycloalkyl groups include perhydronaphthyl, adamantyl and norbornyl groups bridged to a cyclic group or spirobicyclic groups e.g spiro (4,4) non-2-yl. The term "cycloalkyl" is to be understood as preferably meaning a $C_3$-$C_{12}$ cycloalkyl group, more particularly a saturated cycloalkyl group of the indicated ring size, meaning e.g. a cyclopropyl, cyclobutyl, cyclopentyl, cyclohexyl, cycloheptyl, cyclooctyl, cyclononyl, or cyclodecyl group; and also as meaning an unsaturated cycloalkyl group containing one or more double bonds in the C-backbone, e.g. a $C_3$-$C_{10}$ cycloalkenyl group, such as, for example, a cyclopropenyl, cyclobutenyl, cyclopentenyl, cyclohexenyl, cycloheptenyl, cyclooctenyl, cyclononenyl, or cyclodecenyl group, wherein the linkage of said cycloalkyl group to the rest of the molecule can be provided to the double or single bond; and also as meaning such a saturated or unsaturated cycloalkyl group being optionally substituted one or more times, independently of each other, with a $C_1$-$C_6$ alkyl group and/or a halogen and/or an OR group and/or a NR'R" group; such as, for example, a 2-methyl-cyclopropyl group, a 2,2-dimethylcyclopropyl group, a 2,2-dimethylcyclobutyl group, a 3-hydroxycyclopentyl group, a 3-hydroxycyclohexyl group, a 3-dimethylaminocyclobutyl group, a 3-dimethylaminocyclopentyl group or a 4-dimethylaminocyclohexyl group.

The term "thio" refers to a group containing a sulfur linkage.

Related to "thio" is the term "alkylthio" which denotes an alkyl group attached via sulfur linkage to the rest of the molecule. Representative examples of those groups are methiol and ethiol.

The term "halo" refers to radicals of fluorine, chlorine, bromine and iodine.

The term "aryl" refers to aromatic radicals having in the range of 6 up to 14 carbon atoms such as phenyl, naphthyl, tetrahydronaphthyl, indanyl, biphenyl being optionally further substituted by an $C_1$-$C_6$ alkyl group and/or a halogen atom.

The term "heteroaryl" refers to a heterocyclic ring radical as defined herein which is aromatic being optionally further substituted by an $C_1$-$C_6$ alkyl group and/or a halogen atom. The heteroaryl ring radical may be attached to the main structure at any heteroatom or carbon atom that results in the creation of a stable structure.

The term "amino" refers to a group having the functional group $-NH_2$. The group can be, e.g. branched or unbranched have a carbon backbone of $C_1$ to $C_{12}$, possibly more.

The term "amide" refers to an organic compound that contains the functional group $-C(O)NR'R"$.

The term "aryloxyl" refers to an aryl as defined herein attached via oxygen linkage to the rest of the molecule. Representative examples of those groups are methylphenoxy and ethylphenoxy.

The term "sulfonamido" refers to a group having the functional group —SO$_2$NR'R". Examples are selected from —SO$_2$NH$_2$, —SO$_2$NR-substituted alkyl, —SO$_2$NR-alkenyl, —SO$_2$NR-substituted alkenyl, —SO$_2$NR-alkynyl, —SO$_2$NR-substituted alkynyl, —SO$_2$NR-aryl, —SO$_2$NR-substituted aryl, —SO$_2$NR-heteroaryl, and —SO$_2$NR-substituted heteroaryl.

The preferred aromatic group is phenyl, para(4-)substituted phenyl, or biphenyl. The preferred acidic group (X) is a phosphonate resulting in compounds of formula (V) or (VI)

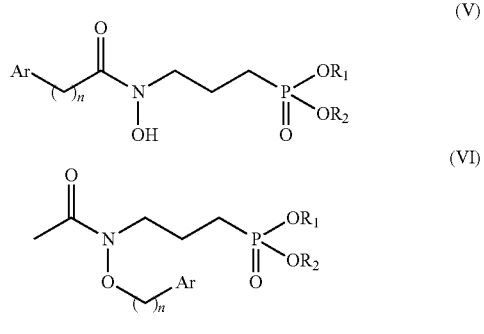

where R$_1$ and R$_2$ are independently alkyl, aryl, pivaloyl, substituted carbonyl, or the like. The R$_1$ and R$_2$ substituents can be added to enhance whole cell penetration of the compounds across mycobacterial and bacterial cell walls. These esters can be hydrolyzed once inside the cell to reveal the acidic group, which is a component of the active compound. Preferably, R$_1$ and R$_2$ are independently ethyl, pivalate, methyl pivalate, methyl benzoate, related esters thereof, or H. In the case where R$_1$ and R$_2$ are H, the results are the compounds of formula (III) or (IV). In the case where R$_1$ and R$_2$ ethyl, the results are the compounds of formula (VII) or (VIII).

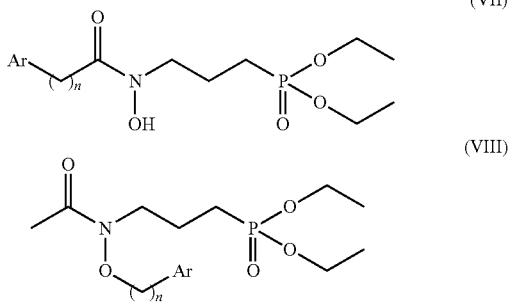

Figure 1:
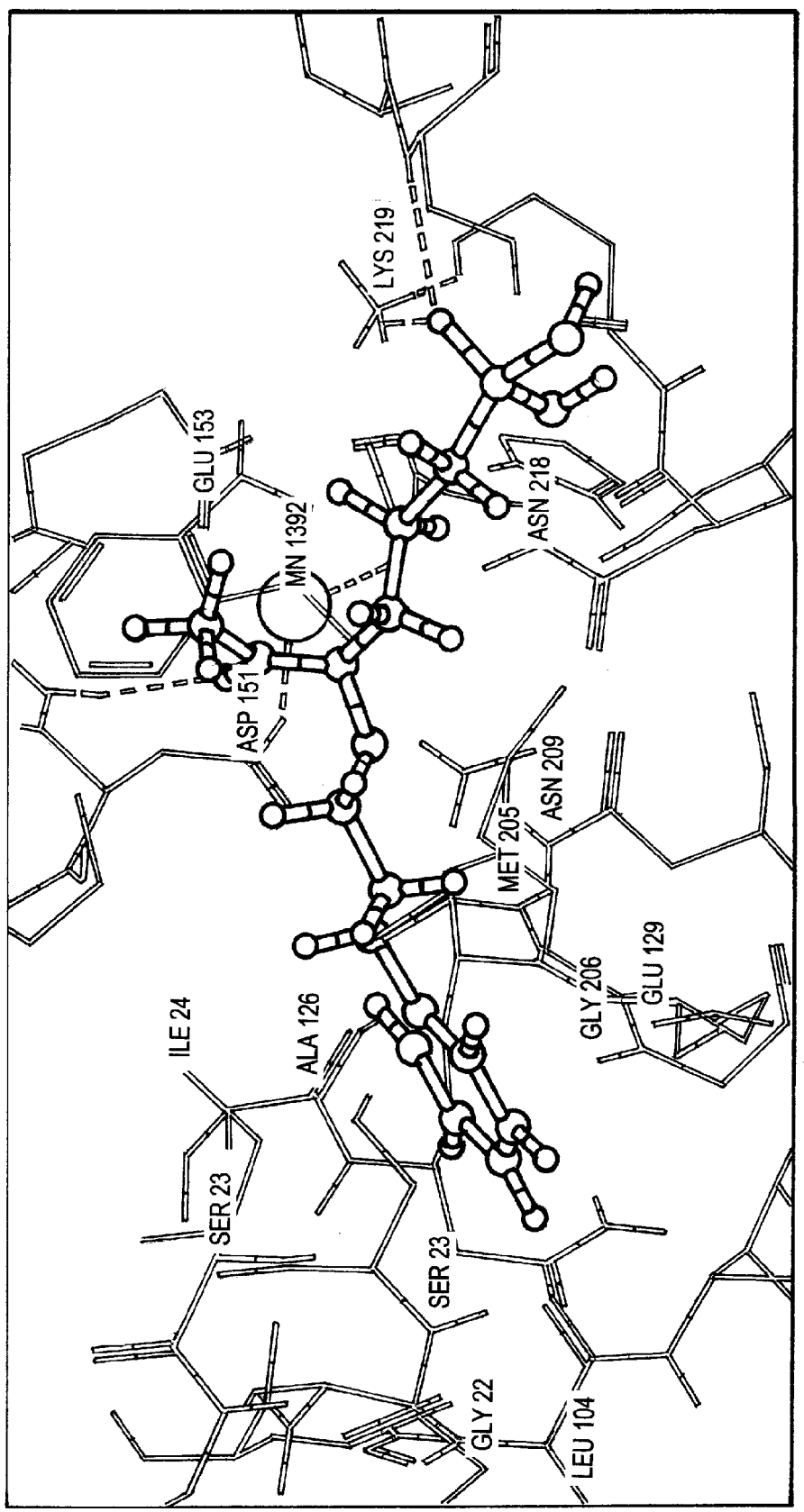
FIG. 1 is a model showing a computer docking solution for a compound of the present invention with 1-deoxy-D- xylulose-5-phosphate reductoisomerase (Dxr) from *Mycobacterium tuberculosis* (Mtb).

The compounds of the present invention inhibit Dxr by binding the enzyme at two binding sites, the NADP+ and the fosmidomycin binding sites. FIG. 1 shows a computer solution of the binding of a compound of the present invention with Dxr. The result shows the compound bridging the NADP+ and the fosmidomycin binding sites which is predicted to result in an inhibitor with improved affinity when compared to fosmidomycin or FR900098.

The compounds of the present invention can be made using methods known in the art. In one embodiment, the compounds of formula (VII) can be synthesized using the process outlined in Scheme 1.

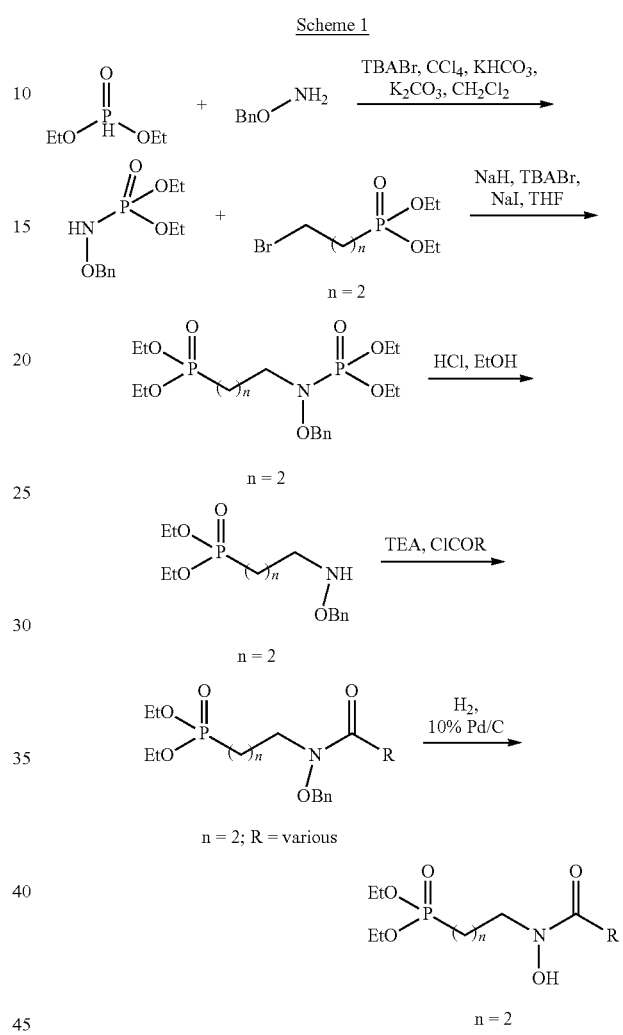

In Scheme 1, Et designates an ethyl group, Bn designates a benzyl group, and R designates —(CH$_2$)$_n$—Ar. O-Benzylhydroxylamine is combined with diethyl phosphite in the presence of tetrabutylammonium bromide, carbon tetrachloride, potassium hydrogen carbonate and potassium carbonate in methylene chloride to give the diethyl phosphoramide ester. This ester is combined with a diethyl bromoalkylphosphonate ester in the presence of sodium hydride, tetrabutylammonium bromide and sodium iodide in tetrahydrofuran to give the alkylphosphonate-substituted phosphoramidate. The phosphoramide is hydrolyzed under acidic conditions using a 5 minute exposure of hydrochloric acid at reflux. The resulting amine is then acylated using the appropriate acyl halide in triethylamine. Removal of the benzyl protecting group is accomplished using catalytic hydrogenation at room temperature.

The compounds of formula (VIII), formula (IV) and its salts can be synthesized using the process outlined in Scheme 2.

Scheme 2

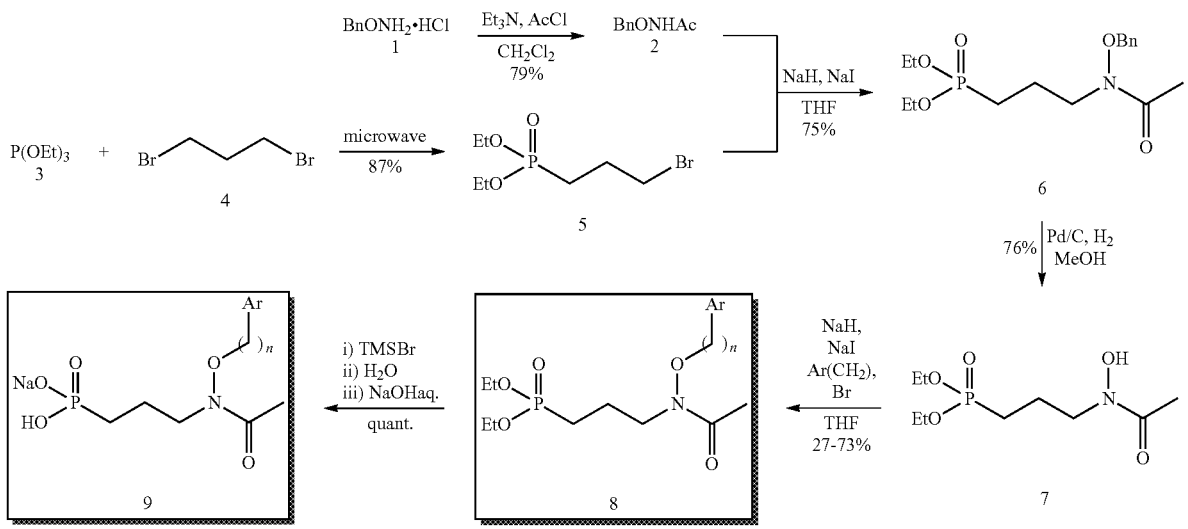

In Scheme 2, O-Benzylhydroxylamine is acylated using acetyl chloride and triethylamine. Triethylphosphite is reacted with 1,3-dibromopropane (preferably solventless) in the microwave at full power for 7 minutes to give diethyl 3-bromopropylphosphonate 5. Compounds 2 and 5 are combined in the presence of sodium hydride and sodium iodide to give compound 6. The benzyl protecting group is removed using catalytic hydrogenation conditions at room temperature, giving compound 7. Compound 7 is alkylated using sodium hydride, sodium iodide and the appropriate alkyl bromide in THF to give compound 8. This step incorporates the aryl ring to make the compound of formula (VIII). Hydrolysis of the diethyl ester is accomplished using trimethylsilylbromide, followed by water, to produce the compound of formula (IV). The sodium salt can then be generated by addition of NaOH (aq) to give compound 9 which is a sodium salt of the compound of formula (IV).

Other compounds of the present invention can similarly be synthesized. For example, to make the compounds of formula (III), the final compound of Scheme 1 can be hydrolyze, e.g. by trimethylsilyl bromide (TMSBr) and H$_2$O (similar to the last step of Scheme 2). Other alkyl esters can also be made (instead of ethyl) by alkylating the hydrolysis product (formula (III)), e.g. by reacting the hydrolysis product with an alkyl halide and a suitable base such as triethylamine.

Similarly, the compound of formula (IV) can be made by modifying Scheme 2 to hydrolyze the compound of formula (VIII) (shown as 8 in Scheme 2), e.g. by TMSBr and H$_2$O. Other alkyl esters can also be made (instead of ethyl) by alkylating the hydrolysis product (formula (IV)), e.g. by reacting the hydrolysis product with an alkyl halide and a suitable base such as triethylamine. One skilled in the art would be able to modify Scheme 1 and Scheme 2 to synthesize various compounds of the present invention without undue experimentation.

The compounds of the present invention can also form salts by base addition. The salts can be formed by treating the compounds of the present invention with an appropriate base. The base includes, but is not limited to, inorganic bases, such as sodium hydroxide, potassium hydroxide, aluminum hydroxide, calcium hydroxide, magnesium hydroxide, lithium hydroxide, and zinc hydroxide; or organic bases, such as ammonia, pyridine, diethanolamine, ethylenediamine, and meglumine. The preferred salts for the present invention are sodium, potassium, and ammonium salts.

The compounds of the present invention preferably inhibit Dxr by contacting the enzyme and binding the enzyme at two sites: the NADP+ and the fosmidomycin binding sites. Preferably, contact of the compounds and Dxr is facilitated in solution. For example, a compound of the present invention can be added to a solution containing Dxr: and the activity of Dxr is determined after the compound is given sufficient time to bind the enzyme. Dxr activity can be measured by monitoring NADPH turnover. As the reaction progresses, NADPH is consumed, a process that is monitored by a decrease in UV absorbance (340 nm). When an inhibitor is present, the turnover of NADPH is slowed. Thus, by observing the change in NADPH over time of Dxr with and without the presence of the compound of the present invention, it can be determined whether the compound inhibits Dxr.

Accordingly, an embodiment of the present invention relates to methods for screening compounds for inhibiting Dxr. The method contains the steps of a) making the compounds of the present invention; and b) screening those compounds for its ability to inhibit Dxr. The screening step involves contacting each of the compounds with Dxr, preferably in solution and determining the enzyme activity. The enzyme activity can be determined by determining the IC50 of the compound or the enzyme activity remaining at a predetermined concentration of the compound. Compounds that highly inhibit Dxr are selected as candidates for antibiotics and further tested for their antibiotic properties.

In an embodiment, the compounds of the present invention are used as antibiotics, preferably for treating Mtb infections. Accordingly, the compounds of the present invention may be modified in order to improve their efficacy. Such modification of the compounds may be used to decrease toxicity, increase bioavailability, or modify biodistribution. Apart from modification, bioavailability or biodistribution may also be improved by the use of excipients in the pharmaceutical formulation.

In yet another embodiment, the present invention relates to pharmaceutical compositions containing at least one of the compounds of the present invention alone or in combination with other therapeutic agents or active ingredients. Regardless of whether the active component of the pharmaceutical composition is a compound alone or in combination with another active agent, each of these preparations is in some aspects provided in a pharmaceutically acceptable form optionally combined with a pharmaceutically acceptable carrier. Those compositions are administered by any methods that achieve their intended purposes. Individualized amounts and regimens for the administration of the compositions for the treatment of the given disorder are determined readily by those with ordinary skill in the art using assays that are used for the diagnosis of the disorder and determining the level of effect a given therapeutic intervention produces.

It is understood that the suitable dose of a composition according to the present invention will depend upon the age, health and weight of the recipient, kind of concurrent treatment, if any, frequency of treatment, and the nature of the effect desired. However, the dosage is tailored to the individual subject, as is understood and determinable by one of skill in the art, without undue experimentation. This typically involves adjustment of a standard dose, e.g., reduction of the dose if the patient has a low body weight.

The total dose of therapeutic agent may be administered in multiple doses or in a single dose. In certain embodiments, the compositions are administered alone, in other embodiments the compositions are administered in conjunction with other therapeutics directed to the disease or directed to other symptoms thereof.

In some aspects, the pharmaceutical compositions of the invention are formulated into suitable pharmaceutical compositions, i.e., in a form appropriate for applications in the therapeutic intervention of a given disease. Methods of formulating proteins and peptides for therapeutic administration also are known to those of skill in the art. Administration of those compositions according to the present invention will be via any common route so long as the target tissue is available via that route. Preferably, those compositions are formulated as an injectable. Appropriate routes of administration for the present invention may include oral, subcutaneous, intravenous, intradermal, intramuscular, intramammary, intraperitoneal, intrathecal, intraocular, retrobulbar, intrapulmonary (e.g., term release), aerosol, sublingual, nasal, anal, vaginal, or transdermal delivery, or by surgical implantation at a particular site is also used, particularly when oral administration is problematic. The treatment may consist of a single dose or a plurality of doses over a period of time.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. In some aspects, the carrier is a solvent or dispersion medium containing, for example, water, ethanol, polyol (for example, glycerol, propylene glycol, and liquid polyethylene glycol, and the like), suitable mixtures thereof, and vegetable oils. The proper fluidity is maintained, for example, by the use of a coating, such as lecithin, by the maintenance of the required particle size in the case of dispersion and by the use of surfactants. The prevention of the action of microorganisms is brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions is brought about by the use in the compositions of agents delaying absorption, for example, aluminum monostearate and gelatin.

Sterile injectable solutions are prepared by incorporating the compounds of the present invention in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution is suitably buffered if necessary and the liquid diluent first rendered isotonic with sufficient saline or glucose. These particular aqueous solutions are especially suitable for intravenous, intramuscular, subcutaneous and intraperitoneal administration. Those of ordinary skill in the art will readily optimize effective dosages and administration regimens as determined by good medical practice and the clinical condition of the individual patient.

The frequency of dosing will depend on the pharmacokinetic parameters of the compounds and the routes of administration. The optimal pharmaceutical formulation will be determined by one of skill in the art depending on the route of administration and the desired dosage. Such formulations may influence the physical state, stability, rate of in vivo release and rate of in vivo clearance of the administered agents. Depending on the route of administration, a suitable dose is calculated according to body weight, body surface areas or organ size. The availability of animal models is particularly useful in facilitating a determination of appropriate dosages of a given therapeutic. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

Typically, appropriate dosages are ascertained through the use of established assays for determining blood levels in conjunction with relevant dose response data. The final dosage regimen will be determined by the attending physician, considering factors which modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions. Those studies, however, are routine and within the level of skilled persons in the art.

It will be appreciated that the pharmaceutical compositions are useful in fields of human medicine and veterinary medicine. Thus, the subject to be treated is a mammal, such as a human or other mammalian animal. For veterinary purposes, subjects include for example, farm animals including cows, sheep, pigs, horses and goats, companion animals such as dogs and cats, exotic and/or zoo animals, and laboratory animals including mice, rats, rabbits, guinea pigs and hamsters.

Without further description, it is believed that one of ordinary skill in the art can, using the preceding description and the following illustrative examples, make and utilize the compounds and methods of the present invention. The following examples are given to illustrate the present invention. It should be understood that the invention is not to be limited to the specific conditions or details described in those examples.

Example 1

The following compounds have been synthesized and tested for their activities against bacteria (Table 1) and their abilities to inhibit Dxr (Table 2). MIC is determined as described in Yendapally et al. (*Journal of Medicinal Chemistry* 2008, 51, 1487); and IC50 is determined as described in Henriksson et al. (*Journal of Biological Chemistry* 2007, 282, 19905).

TABLE 1

| Compound name | Structure | Acinetobacter | E. coli k12 | E. coli tolc | Klebsiella | P. aeruginosa | S. pneumonia | B. anthracis | E. faecalis | S. aureus (MSSA) | MRSA NRS 70 | H37 Rv |
|---|---|---|---|---|---|---|---|---|---|---|---|---|
| ERJ 58 | 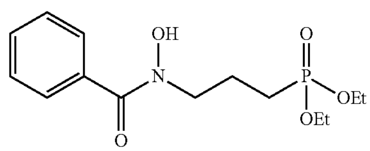 [SMILES: CCOP(=O)(CCCN(O)C(=O)c1ccccc1)OCC] | >200 | >200 | >200 | >200 | >200 | >200 | >200 | >200 | >200 | >200 | >200 |
| ERJ 70 | 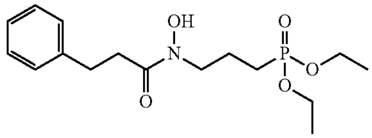 [SMILES: CCOP(=O)(CCCN(O)C(=O)CCc1ccccc1)OCC] | >200 | >200 | >200 | >200 | >200 | >200 | >200 | >200 | >200 | >200 | >200 |
| ERJ 79 | 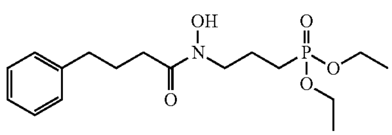 [SMILES: CCOP(=O)(CCCN(O)C(=O)CCCc1ccccc1)OCC] | >200 | >200 | >200 | >200 | >200 | >200 | >200 | >200 | 100 | 50 | >200 |
| ERJ 91 | 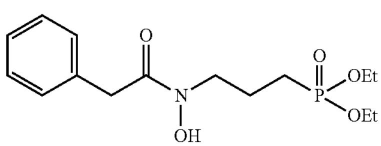 [SMILES: CCOP(=O)(CCCN(O)C(=O)Cc1ccccc1)OCC] | >200 | >200 | >200 | >200 | >200 | >200 | >200 | >200 | 100 | 50 | >200 |
| ERJ 93 | 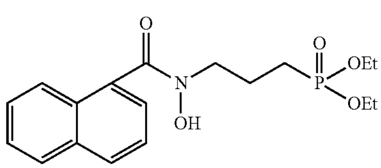 [SMILES: CCOP(=O)(CCCN(O)C(=O)c1cccc2ccccc12)OCC] | >200 | >200 | >200 | >200 | >200 | >200 | 200 | 200 | 100 | 50 | >200 |
| ERJ 96 | 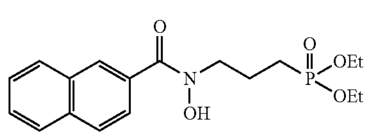 [SMILES: CCOP(=O)(CCCN(O)C(=O)c1ccc2ccccc2c1)OCC] | >200 | >200 | >200 | >200 | >200 | >200 | >200 | >200 | >200 | >200 | >200 |
| ERJ 104 | 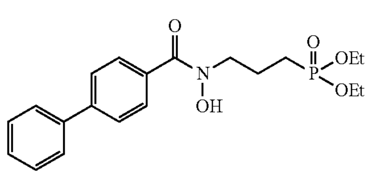 [SMILES: CCOP(=O)(CCCN(O)C(=O)c1ccc(-c2ccccc2)cc1)OCC] | >200 | >200 | 100 | >200 | >200 | >200 | >200 | >200 | 100 | 100 | >200 |

TABLE 1-continued

| Compound name | Structure | Acinetobacter | E. coli k12 | E. coli tolc | Klebsiella | P. aeruginosa | S. pneumonia | B. anthracis | E. faecalis | S. aureus (MSSA) | MRSA NRS 70 | H37 Rv |
|---|---|---|---|---|---|---|---|---|---|---|---|---|
| ERJ 112 | 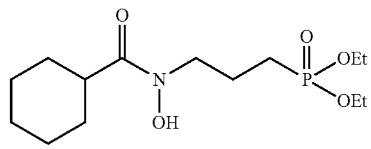 [SMILES: CCOP(=O)(CCCN(O)C(=O)C1CCCCC1)OCC] | | | | | | | | | | | |
| GSJ 20 (Rotamer B) | 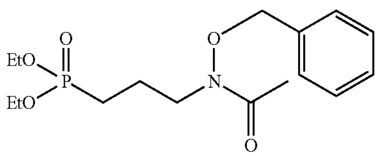 [SMILES: CCOP(=O)(CCCN(OCc1ccccc1)C(C)=O)OCC] | >200 | >200 | >200 | >200 | >200 | >200 | >200 | >200 | >200 | >200 | >200 |
| GSJ 25 | 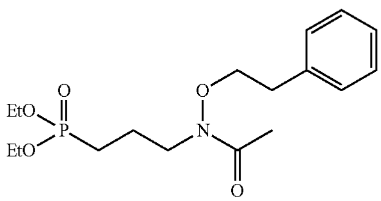 [SMILES: CCOP(=O)(CCCN(OCCc1ccccc1)C(C)=O)OCC] | >200 | >200 | >200 | >200 | >200 | >200 | >200 | >200 | >200 | >200 | >200 |
| GSJ 26 | 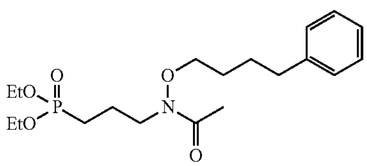 [SMILES: CCOP(=O)(CCCN(OCCCCc1ccccc1)C(C)=O)OCC] | >200 | >200 | 200 | >200 | >200 | >200 | >200 | 200 | 100 | 200 | Some act 200 |
| GSJ 27 | 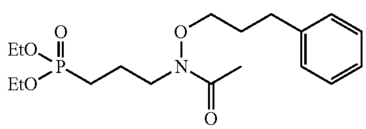 [SMILES: CCOP(=O)(CCCN(OCCCc1ccccc1)C(C)=O)OCC] | >200 | >200 | >200 | >200 | >200 | >200 | >200 | >200 | >200 | >200 | >200 |
| GSJ 28 | 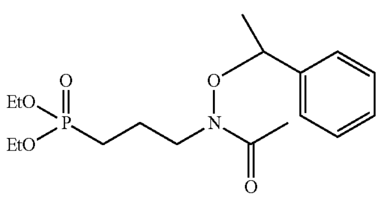 [SMILES: CCOP(=O)(CCCN(OC(C)c1ccccc1)C(C)=O)OCC] | >200 | >200 | >200 | >200 | >200 | >200 | >200 | >200 | 100 | 50 | >200 |
| GSJ 30 | 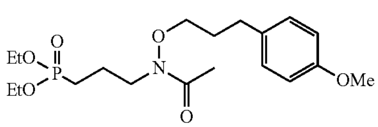 [SMILES: CCOP(=O)(CCCN(OCCCc1ccc(OC)cc1)C(C)=O)OCC] | >200 | >200 | >200 | >200 | >200 | >200 | >200 | >200 | >200 | >200 | >200 |
| GSJ 31 | 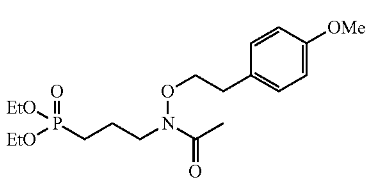 [SMILES: CCOP(=O)(CCCN(OCCc1ccc(OC)cc1)C(C)=O)OCC] | >200 | >200 | >200 | >200 | >200 | >200 | >200 | >200 | 200 | 50 | >200 |

(MIC = minimum inhibitory concentration)

TABLE 2

| Compound name | Structure | IC50 (ug/ml) | IC50 (uM) |
|---|---|---|---|
| GSJ 51 | (3-phenylpropanoyl-N-hydroxy aminopropyl phosphonic acid) | 0.84 | 2.72 |
| GSJ 52 | (4-phenylbutanoyl-N-hydroxy aminopropyl phosphonic acid) | 1.01 | 3.12 |
| GSJ 55 | (phenylacetyl-N-hydroxy aminopropyl phosphonic acid) | 2.21 | 7.49 |
| GSJ 56 | (2-naphthoyl aminopropyl phosphonic acid) | (90%)* | |
| GSJ 58 | (1-naphthoyl-N-hydroxy aminopropyl phosphonic acid, Na salt) | | |
| GSJ 59 | (biphenyl-4-carbonyl-N-hydroxy aminopropyl phosphonic acid, Na salt) | | |
| GSJ 60 | (benzoyl-N-hydroxy aminopropyl phosphonic acid, Na salt) | | |
| GSJ 62 | (N-acetyl-N-(2-(4-methoxyphenyl)ethoxy) aminopropyl phosphonic acid, Na salt) | (85%)* | |

TABLE 2-continued

| Compound name | Structure | IC50 (ug/ml) | IC50 (uM) |
|---|---|---|---|
| GSJ 63 | 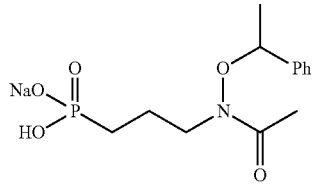 | 52.00 | 160.87 |
| GSJ 64 | 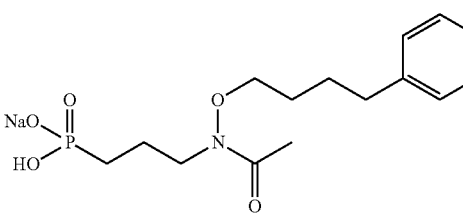 | (100%)* | |
| GSJ 65 | 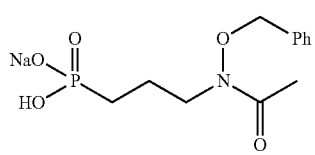 | (83%)* | |
| GSJ 67 | 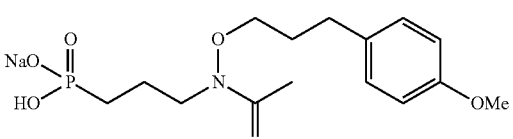 | (64%)* | |
| ERJ 116 | 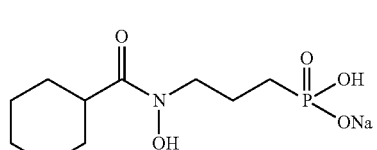 | | |

*Data in parentheses indicate percent enzyme activity remaining at 100 ug/ml compound.

Table 3 shows several compounds, along with isoniazid and fosmidomycin, and their minimum inhibitory concentrations (MIC) against Mtb H37Rv (ATCC 27294) in 7119 and GAST/Fc media. The MIC assay was performed as described in Kim et al. (*Journal of Medicinal Chemistry* 2009, 52:1317-1328).

TABLE 3

| No. | Structure | MIC 7H9 (μg/mL) | MIC GAST/Fe (μg/mL) |
|---|---|---|---|
| Isoniazid | 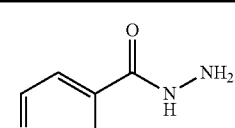 | 0.04 | 0.02 |
| Fosmidomycin | 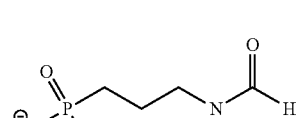 | >500 | >500 |

TABLE 3-continued

| No. | Structure | MIC 7H9 (μg/mL) | MIC GAST/Fe (μg/mL) |
|---|---|---|---|
| 5b | (formyl-N(OH)-CH2CH2-P(O)(OEt)2) | >500 | >500 |
| 5c | (formyl-N(OH)-(CH2)3-P(O)(OEt)2) | 250 | IP |
| 5f | (acetyl-N(OH)-CH2CH2-P(O)(OEt)2) | >500 | >500 |
| 9d | (acetyl-N(OH)-(CH2)4-P(O)(OEt)2) | IP | IP |
| 9e | (acetyl-N(OH)-(CH2)5-P(O)(OEt)2) | IP | IP |
| 9a | (benzoyl-N(OH)-(CH2)3-P(O)(OEt)2) | >500 | 31.25 |
| 9b | (PhCH2CH2C(O)-N(OH)-(CH2)3-P(O)(OEt)2) | IP | IP |
| 9c | (Ph(CH2)3C(O)-NH-(CH2)3-P(O)(OEt)2) | IP | IP |

(IP = in progress)

Table 4 shows several compounds that were synthesized, and their minimum inhibitory concentrations (MIC) against Mtb and their ability to inhibit Mtb Dxr (IC50).

TABLE 4

| Name | Compound | Mtb MIC (ug/mL) | Mtb Dxr IC$_{50}$ (ug/mL) |
|---|---|---|---|
| GSJ21 | (EtO)$_2$P(O)-CH$_2$CH$_2$CH$_2$-N(OH)-C(O)CH$_3$ | >200 | |
| GSJ20-rotamer B | (EtO)$_2$P(O)-CH$_2$CH$_2$CH$_2$-N(OCH$_2$Ph)-C(O)CH$_3$ | >200 | |
| GSJ25 | (EtO)$_2$P(O)-CH$_2$CH$_2$CH$_2$-N(O(CH$_2$)$_2$Ph)-C(O)CH$_3$ | >200 | |
| GSJ27 | (EtO)$_2$P(O)-CH$_2$CH$_2$CH$_2$-N(O(CH$_2$)$_3$Ph)-C(O)CH$_3$ | >200 | |
| GSJ26 | (EtO)$_2$P(O)-CH$_2$CH$_2$CH$_2$-N(O(CH$_2$)$_4$Ph)-C(O)CH$_3$ | SA 200 | |
| GSJ31 | (EtO)$_2$P(O)-CH$_2$CH$_2$CH$_2$-N(O(CH$_2$)$_2$-C$_6$H$_4$-OMe)-C(O)CH$_3$ | >200 | |
| GSJ30 | (EtO)$_2$P(O)-CH$_2$CH$_2$CH$_2$-N(O(CH$_2$)$_3$-C$_6$H$_4$-OMe)-C(O)CH$_3$ | >200 | |
| GSJ28 | (EtO)$_2$P(O)-CH$_2$CH$_2$CH$_2$-N(OCH(CH$_3$)Ph)-C(O)CH$_3$ | >200 | |

TABLE 4-continued

| Name | Compound | Mtb MIC (ug/mL) | Mtb Dxr IC$_{50}$ (ug/mL) |
| --- | --- | --- | --- |
| GSJ70 | | | 400 (7H9)<br>200 (GAST) |
| GSJ71 | | | ≥400 (7H9)<br>200-400 (GAST) |
| GSJ72 | | | 200 (7H9)<br>100 (GAST) |
| GSJ73 | | | 200 (7H9)<br>100 (GAST) |
| GSJ80 | | | 200-400 |
| GSJ82 | | | ≥400 (7H9)<br>no result for GAST |
| GSJ100 | | | 100 |

TABLE 4-continued
| Name | Compound | Mtb MIC (ug/mL) | Mtb Dxr IC$_{50}$ (ug/mL) |
|---|---|---|---|
| GSJ101 | 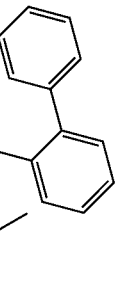 | 200-400 | |
| GSJ102 | 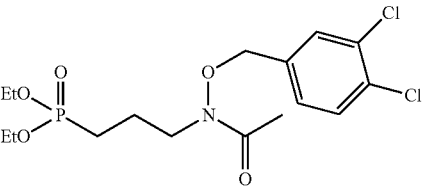 [SMILES: CCOP(=O)(CCCN(OCc1ccc(Cl)c(Cl)c1)C(C)=O)OCC] | 200 | |
| GSJ109 | 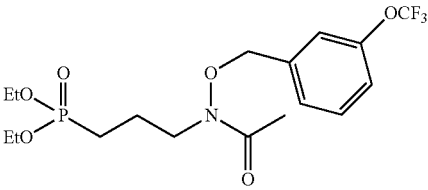 [SMILES: CCOP(=O)(CCCN(OCc1cccc(OC(F)(F)F)c1)C(C)=O)OCC] | 400 | |
| GSJ110 | 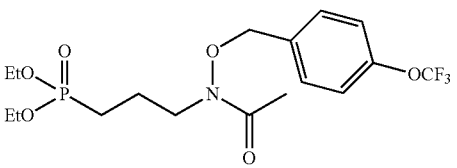 [SMILES: CCOP(=O)(CCCN(OCc1ccc(OC(F)(F)F)cc1)C(C)=O)OCC] | 400 | |
| GSJ111 | 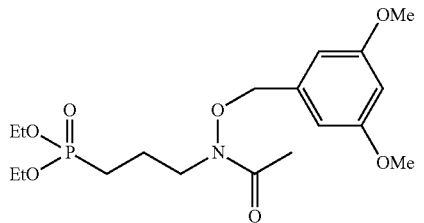 [SMILES: CCOP(=O)(CCCN(OCc1cc(OC)cc(OC)c1)C(C)=O)OCC] | >400 | |
| GSJ112 | 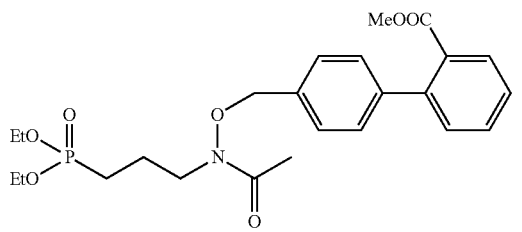 [SMILES: CCOP(=O)(CCCN(OCc1ccc(-c2ccccc2C(=O)OC)cc1)C(C)=O)OCC] | 400 | |
| GSJ113 | 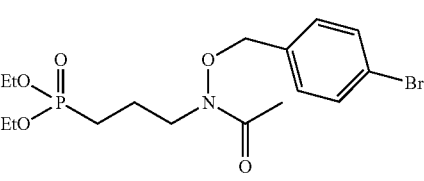 [SMILES: CCOP(=O)(CCCN(OCc1ccc(Br)cc1)C(C)=O)OCC] | 400 | |

TABLE 4-continued
| Name | Compound | Mtb MIC (ug/mL) | Mtb Dxr IC$_{50}$ (ug/mL) |
|---|---|---|---|
| GSJ114 | 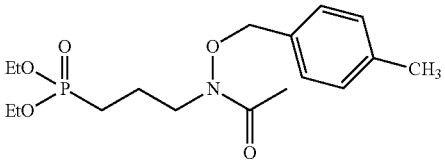 [SMILES: CCOP(=O)(CCCN(OCc1ccc(C)cc1)C(C)=O)OCC] | | >400 |
| GSJ115 | 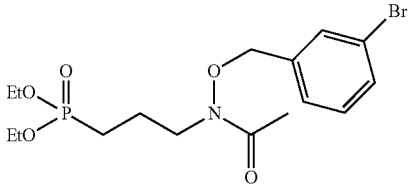 [SMILES: CCOP(=O)(CCCN(OCc1cccc(Br)c1)C(C)=O)OCC] | | 400 |
| GSJ116 | 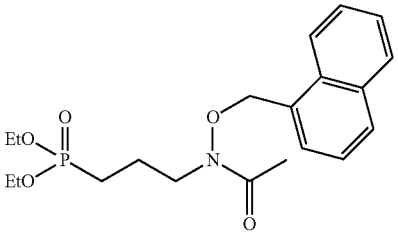 [SMILES: CCOP(=O)(CCCN(OCc1cccc2ccccc12)C(C)=O)OCC] | | 400 |
| GSJ89 | 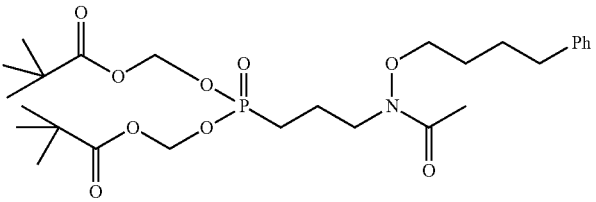 [SMILES: CC(=O)N(CCCP(=O)(OCOC(=O)C(C)(C)C)OCOC(=O)C(C)(C)C)OCCCCc1ccccc1] | 12.5 (7H9) 6.25-12.5 (GAST) | |
| GSJ92 | 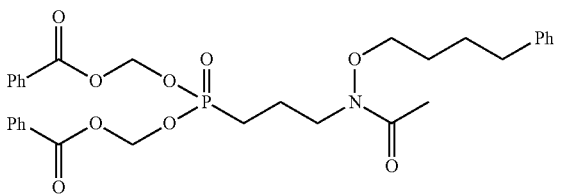 [SMILES: CC(=O)N(CCCP(=O)(OCOC(=O)c1ccccc1)OCOC(=O)c1ccccc1)OCCCCc1ccccc1] | 25 (7H9) no result for GAST | |
| GSJ96 | 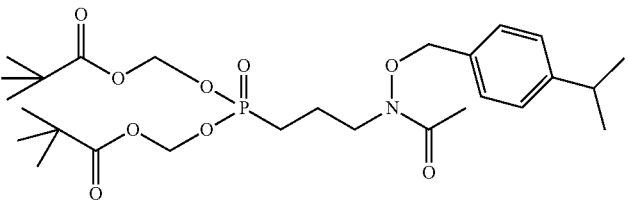 [SMILES: CC(=O)N(CCCP(=O)(OCOC(=O)C(C)(C)C)OCOC(=O)C(C)(C)C)OCc1ccc(C(C)C)cc1] | 12.5 | |
| GSJ97 | 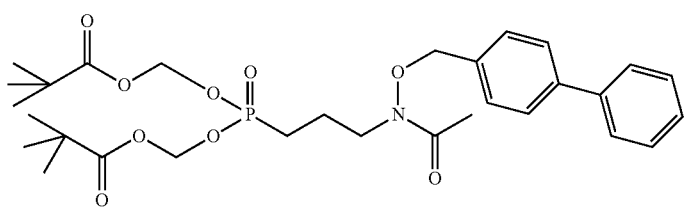 [SMILES: CC(=O)N(CCCP(=O)(OCOC(=O)C(C)(C)C)OCOC(=O)C(C)(C)C)OCc1ccc(-c2ccccc2)cc1] | 12.5 | |

TABLE 4-continued

| Name | Compound | Mtb MIC (ug/mL) | Mtb Dxr IC$_{50}$ (ug/mL) |
|---|---|---|---|
| FR900098 | | >200 | |
| GSJ65 | | >200 | (83%) |
| GSJ78 | | >200 | 31.17 |
| GSJ68 | | 200 | (108%) |
| GSJ64 | | ≥200 (7H9) 200 (GAST) | (103%) |
| GSJ62 | | >200 | (85%) |
| GSJ67 | | 200 | (64%) |
| GSJ63 | | >200 | 52.00 |
| GSJ76 | | 200 (7H9) 25 (GAST) | 17.78 |

TABLE 4-continued

| Name | Compound | Mtb MIC (ug/mL) | Mtb Dxr IC$_{50}$ (ug/mL) |
|---|---|---|---|
| GSJ75 | | >200 | 62.29 |
| GSJ74 | | 25-50 | 24.91 |
| GSJ77 | | ≥200 | 16.09 |
| GSJ105 | | >400 | |
| GSJ93 | | >400 | |
| GSJ106 | | 200-400 | |
| GSJ107 | | 200-400 | |

TABLE 4-continued
| Name | Compound | Mtb MIC (ug/mL) | Mtb Dxr IC$_{50}$ (ug/mL) |
|---|---|---|---|
| GSJ108 | 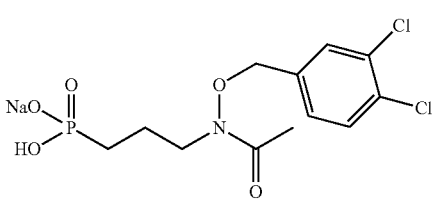 | | >400 |
| GSJ124 | 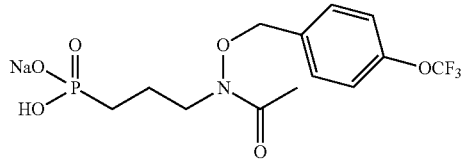 | | |
| GSJ125 | 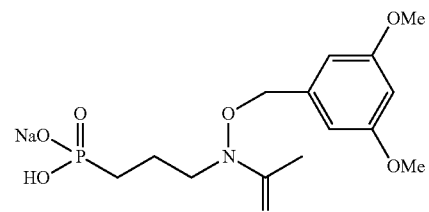 | | |
| GSJ126 | 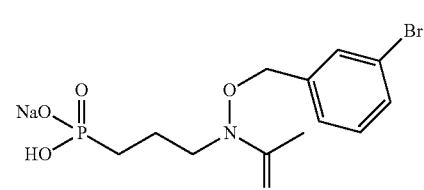 | | |
| GSJ127 | 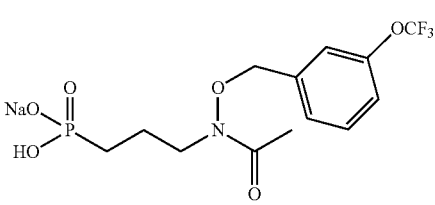 | | |
| GSJ128 | 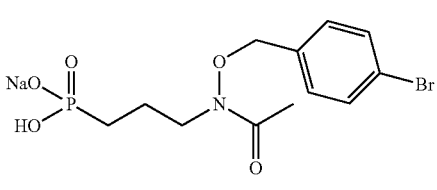 | | |
| GSJ120 | 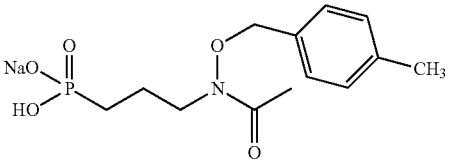 | | |

TABLE 4-continued

| Name | Compound | Mtb MIC (ug/mL) | Mtb Dxr IC$_{50}$ (ug/mL) |
|---|---|---|---|
| GSJ131 | | | |
| GSJ51 | | >200 | 0.84 |
| GSJ52 | | >200 | 1.01 |
| GSJ54 | | >200 | 2.78 |
| GSJ55 | | >200 | 2.21 |
| GSJ56 | | >200 | (90%) |
| GSJ57 | | >200 | (87%) |
| ERJ116 | | >200 (7H9) >200 (GAST) | 16.61 |
| ERJ 119 | | >200 (7H9) >200 (GAST) | |

TABLE 4-continued

| Name | Compound | Mtb MIC (ug/mL) | Mtb Dxr IC$_{50}$ (ug/mL) |
|------|----------|-----------------|---------------------------|
| ERJ 123 | | | >400 |
| ERJ 112 | | | >200 (7H9)<br>100 (GAST) |
| ERJ 58 | | | >500 (7H9)<br>31.25 (GAST) |
| ERJ 91 | | | |
| ERJ 70 | | | 3.125 (7H9)<br>>200 (GAST) |
| ERJ 79 | | | 3.125 (7H9)<br>>200 (GAST) |

Without further description, it is believed that one of ordinary skill in the art can, using the preceding description and the following illustrative examples, make and utilize the compounds of the present invention and practice the claimed methods. The following examples are given to illustrate the present invention. It should be understood that the invention is not to be limited to the specific conditions or details described in those examples.

Example 2

We undertook the design and synthesis of two series of compounds with amide- or O-linked substituents appended to the hydroxamate of FR900098 (Chart 1). We present here the initial results of our docking, synthesis, and evaluation of these compounds.

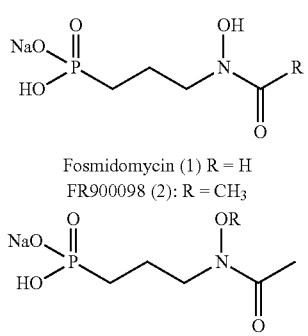

Chart 1. Structures of fosmidomycin, FR900098 and analogs (3-9) examined in this study.

Fosmidomycin (1) R = H
FR900098 (2): R = CH$_3$

3: R = (CH$_2$)$_2$Ph
4: R = (CH$_2$)$_3$Ph
5: R = 4-isopropylbenzyl
6: R = cyclohexylmethyl -continued

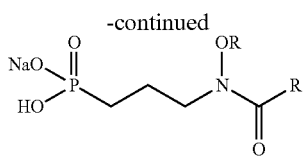

7: R = CH₂Ph
8: R = (CH₂)₃Ph
9: R = cyclohexyl

Experimental Section

Synthesis. General.

$^1$H and $^{13}$C NMR spectra were recorded in CDCl₃ or D₂O on Bruker spectrometer at 200 and 50 MHz, respectively, with TMS as an internal standard. Mass spectra were measured in the ESI mode on an LC-MS (Agilent 1100). High-resolution mass spectroscopy (HRMS) spectra were obtained from the Mass Spectrometry Laboratory. University of Maryland Baltimore County, Baltimore, Md. Thin layer chromatography (TLC) was performed on Merck 60 F$_{254}$ silica gel plates and flash column chromatography was carried out using Merck silica gel 60 (33-70 μm). All reagents were purchase from commercial suppliers and used without further purification. THF and dichloromethane were distilled under argon immediately before use, respectively from sodium/benzophenone and calcium hydride. Purity of compounds (>95%) was determined by $^1$H/$^{13}$C NMR, LC-DAD-MS and HRMS.

General Procedure for the Deprotection of Ether and Amide Ligands 3-9.

To a solution of diethyl 3-(N-(aryloxy)acetamido)propylphosphonate or diethyl 3-(N-hydroxy-arylamido)propylphosphonate (1 eq) in CH₂Cl₂ (1.7 mL/mmol of phosphonate) at 0° C. was added bromotrimethylsilane (8 eq) dropwise. The reaction mixture was stirred overnight at room temperature. Ethyl bromide and excess silylating agent were removed by rotary evaporation at room temperature. The concentrate was solubilized in dry CH₂Cl₂ and evaporated again (×2). H₂O was added to the residue, and the mixture was stirred overnight at room temperature. The solution was filtered (except for products with a low solubility in water) and concentrated in vacuo at 50° C. The crude acid was rapidly neutralized with aqueous NaOH (1 eq) and the mixture was stirred overnight at room temperature. The reaction mixture was concentrated in vacuo at 50° C. No further purification was necessary.

Sodium hydrogen 3-(N-(phenethyloxy)acetamido) propylphosphonate (3)

Prepared from 17a (45 mg, 0.126 mmol). Quantitative yield (light yellow solid). $^1$H NMR (200 MHz, D₂O) δ (24:76 mixture of two conformers) 7.47-7.21 (m, 5H), 4.16 (t, 2H, J=5.9 Hz), 3.54 (t, 2H, J=6.3 Hz), 3.09-2.98 (m, 24/100 of 2H), 2.93 (t, 76/100 of 2H, J=5.9 Hz), 2.02 (s, 24/100 of 3H), 1.92 (s, 76/100 of 3H), 1.79-1.32 (m, 4H). $^{13}$C NMR (50 MHz, D₂O) δ 174.7, 138.9, 129.6, 129.4, 127.3, 75.5, 46.1 (d, J=18.7 Hz), 34.4, 25.4 (d, J=132.5 Hz), 21.7 (d, J=40.7 Hz), 19.7. HRMS (ESI⁻) m/z calcd for C₁₃H₂₀NNaO₅P [M+H]⁺: 324.0971. Found: 324.0972.

Sodium hydrogen 3-(N-(3-phenylpropoxy)acetamido) propylphosphonate (4)

Prepared from 17b (50 mg, 0.135 mmol). Yield 88% (light yellow solid). $^1$H NMR (200 MHz, D₂O) δ (33:67 mixture of two conformers) 7.46-7.26 (m, 5H), 4.13 (t, 33/100 of 2H, J=6.2 Hz), 3.99 (t, 67/100 of 2H, J=6.2 Hz), 3.69 (t, 67/100 of 2H, J=7.0 Hz), 3.40 (t, 33/100 of 2H, J=7.0 Hz), 2.80 (t, 67/100 of 2H, J=7.6 Hz), 2.79 (t, 33/100 of 2H, J=7.6 Hz), 2.18 (s, 3H), 2.13-1.49 (m, 6H). $^{13}$C NMR (50 MHz, D₂O) δ 174.6, 142.3, 129.3, 129.2, 126.8, 74.2, 46.1 (d, J=19.8 Hz), 31.9, 29.4, 25.6 (d, J=133.6 Hz), 21.8 (d, J=29.7 Hz), 19.8. HRMS (ESI⁺) m/z calcd for C₁₄H₂₂NNaO₅P [M+H]⁺: 338.1128. found: 338.1128.

Sodium hydrogen 3-(N-(4-isopropylbenzyloxy)acetamido)propylphosphonate (5)

Prepared from 17c (50 mg, 0.130 mmol). Yield 61% (white solid). $^1$H NMR (200 MHz, D₂O) δ (75:25 mixture of two conformers) 7.43 (d, 2H, J=8.2 Hz), 7.36 (d, 2H, J=8.2 Hz), 4.92 (s, 2H), 3.83-3.57 (m, 2H), 3.09-2.85 (m, 1H), 2.13 (s, 25/100 of 3H), 2.04 (s, 75/100 of 3H), 1.97-1.72 (m, 2H), 1.62-1.36 (m, 2H), 1.21 (d, 6H, J=6.9 Hz). $^{13}$C NMR (50 MHz, D₂O) δ 175.1, 151.6, 131.8, 130.9, 127.6, 76.4, 46.5 (d, J=18.6 Hz), 34.1, 26.3 (d, J=132.9 Hz), 23.8, 22.3 (d, J=36.9 Hz), 20.0. HRMS (ESI⁺) m/z calcd for C₁₅H₂₄NNaO₅P [M+H]⁺: 352.1284. found: 352.1285.

Sodium hydrogen 3-(N-(cyclohexylmethoxy)acetamido)propylphosphonate (6)

Prepared from 17d (50 mg, 0.143 mmol). Quantitative yield (white solid). $^1$H NMR (200 MHz, D₂O) δ (70:30 mixture of two conformers) 3.86-3.62 (m, 85/100 of 4H), 3.05 (t, 15/100 of 4H, J=7.1 Hz), 2.14 (s, 70/100 of 3H), 2.06 (s, 30/100 of 3H), 2.00-1.42 (m, 9H), 1.39-0.82 (m, 6H). $^{13}$C NMR (50 MHz, D₂O) δ 174.6, 80.2, 45.6 (d, J==20.9 Hz), 36.8, 29.8, 26.5, 25.9, 24.8 (d, J=129.7 Hz), 21.4 (d, J=43.8 Hz), 19.8. HRMS (ESI⁺) m/z calcd for C₁₂H₂₄NNaO₅P [M+H]⁺: 316.1284. found: 316.1285.

Sodium hydrogen 3-(N-hydroxy-2-phenylacetamido) propylphosphonate (7)

Prepared from 22a (50 mg, 0.152 mmol). Quantitative yield (white solid). $^1$H NMR (200 MHz, D₂O) δ (80:20 mixture of two conformers) 7.47-7.23 (m, 5H), 3.85 (s, 80/100 of 2H), 3.79 (s, 20/100 of 2H), 3.68 (t, 80/100 of 2H, J=6.9 Hz), 3.35 (t, 20/100 of 2H, J=7.5 Hz), 1.98-1.72 (m, 2H), 1.72-1.46 (m, 2H). $^{13}$C NMR (50 MHz, D₂O) δ 174.9, 135.6, 129.9, 129.5, 127.7, 49.3 (d, J=19.0 Hz), 39.4, 24.8 (d, J=134.8 Hz), 20.8. HRMS (ESI⁺) m/z calcd for C₁₁H₁₆NNaO₅P [M+H]⁺: 296.0658. found: 296.0658.

Sodium hydrogen 3-(N-hydroxy-4-phenylbutanamido) propylphosphonate (8)

Prepared from 22h (50 mg, 0.140 mmol). Quantitative yield (white solid). $^1$H NMR (200 MHz, D₂O) δ (58:42 mixture of two conformers) 7.42-7.18 (m, 5H), 3.62 (t, 58/100 of 2H, J=6.7 Hz), 3.34 (t, 42/100 of 2H, J=7.3 Hz), 2.64 (t, 2H, J=7.5 Hz), 2.48 (t, 58/100 of 2H, J=7.4 Hz), 2.34 (t, 42/100 of 2H, J=7.4 Hz), 2.06-1.42 (m, 6H), $^{13}$C NMR (50 MHz, D₂O) δ 176.8, 142.8, 129.3, 126.8, 49.2 (d, J=19.0 Hz), 35.2, 31.9, 26.7, 25.1 (d, J=134.4 Hz), 21.0. HRMS (ESI⁺) m/z calcd for C₁₃H₂₀NNaO₅P [M+H]⁺: 324.0971. found: 324.0970.

Sodium hydrogen 3-(N-hydroxycyclohexanecarbox-amido)propylphosphonate (9)

Prepared from 26 (52 mg, 0.162 mmol). Yield 74% (light yellow solid). $^1$H NMR (200 MHz, D$_2$O) δ (59:41 mixture of two conformers) 3.65 (t, 59/100 of 2H, J=6.2 Hz), 3.34 (t, 41/100 of 2H, J=7.5 Hz), 3.12-2.84 (m, 1H), 2.73-2.45 (m, 1H), 2.10-1.45 (m, 8H), 1.44-1.00 (m, 5H). $^{13}$C NMR (50 MHz, D$_2$O) δ 179.9, 49.2 (d, J=19.0 Hz), 40.2, 29.0, 26.0, 25.8, 25.3 (d, J=133.3 Hz), 21.0. HRMS (ESI$^+$) m/z calcd for C$_{10}$H$_{20}$NNaO$_5$P [M+H]$^+$: 288.0971. found: 288.0971.

Results

The design of novel Mtb-specific Dxr inhibitors was performed using computational docking with Glide in Schrödinger 2010. Compounds with the general structures shown in Chart 1 were docked into monomer A of the Mtb Dxr crystal structure of Henriksson et al. (*J. Biol. Chem.* 2007, 282, 19905-19916) (pdb 2jcz, FIG. 2A). A grid of an appropriate size incorporating both the DXP and NADPH binding sites was generated for the docking calculations. NADPH and fosmidomycin were removed from the binding sites, while Mn$^{2+}$ was kept in place. Positional constraints placed the phosphonate moiety of each ligand in the phosphonate binding site of fosmidomycin.

A set of 200 ligands, including fosmidomycin and FR900098, was built and minimized. The analogs retained structural features of fosmidomycin and FR900098 and had added aromatic or cycloalkyl substituents, either on the N-hydroxyl oxygen atom or on the amide carbonyl group. The aromatic group is meant to mimic the pyridyl ring of NADPH. By incorporation of this feature, we hoped to gain affinity to the NADPH pocket, in addition to the adjacent site used by fosmidomycin. Cycloalkyl groups were used to probe the importance of an aryl substituent at this position.

The compounds were successfully docked, and the results show that our ligands adopt the expected binding mode to the protein: similar to fosmidomycin, the hydroxamate moiety chelates the metal ion and the phosphonate group is located in the phosphonate binding site. The compounds bridge the two active sites of the enzyme with the aryl group located in the NADPH pocket (FIGS. 2B and 2C). As expected, the new compounds have higher predicted binding affinity than fosmidomycin, shown by better docking scores (Glide scores or GScores). The more negative GScore indicates a better binding affinity. A representative set of these compounds is shown in Table 5. Our docking results confirm that bridging the substrate and NADPH binding sites of Mtb Dxr is advantageous and should result in more potent inhibitors. In general, the amide-linked compounds are predicted to bind better to the enzyme compared with the O-linked compounds. This may in part be due to differences between the series in binding the divalent cation. The docking experiments indicate these series may hold promise as inhibitors against M. tuberculosis Dxr.

TABLE 5

Inhibition of M. tuberculosis Dxr and predicted binding affinity.

| Compound | R$^1$ | R$^2$ | GScore | % Remaining Enzyme Activity at 100 μg/mL | IC$_{50}$ (μM) |
|---|---|---|---|---|---|
| Fosmidomycin (1) | H | H | −8.03 | — | 0.29 |
| FR900098 (2) | H | CH$_3$ | −8.56 | — | 2.0 |
| 3 | (CH$_2$)$_2$Ph | CH$_3$ | −9.16 | — | 96.4 |
| 4 | (CH$_2$)$_3$Ph | CH$_3$ | −9.44 | 100 | — |
| 5 | 4-isopropylbenzyl | CH$_3$ | −9.57 | — | 50.6 |
| 6 | cyclohexylmethyl | CH$_3$ | −9.32 | — | 197.6 |
| 7 | H | CH$_2$Ph | −10.44 | — | 7.5 |
| 8 | H | (CH$_2$)$_3$Ph | −10.87 | — | 3.1 |
| 9 | H | cyclohexyl | −10.76 | — | 57.8 |

The preparation of these compounds is shown in Schemes 1-3. A new synthetic route was developed for the synthesis of the O-linked compounds 3-6, using known and straight-forward reactions allowing fast access to small, structurally modified molecules in good yield (Scheme 1).

Compound 11 was obtained by acetylation of O-benzyl-hydroxylamine hydrochloride 10, and 3-bromopropylphosphonate 14 was prepared from triethyl phosphite 12 and 1,3-dibromopropane 13, using the Arbuzov reaction under microwave irradiation (Villemin et al. *Phosphorus, Sulfur and Silicon* 1998, 133, 209-213). Compounds 11 and 14 were then combined under basic conditions to give 15, which yielded hydroxylamine 16 alter hydrogenation. The ether ligands 17a-d were obtained by alkylation of intermediate 16 using sodium hydride and the corresponding aryl or alkyl bromide. The four desired monosodium salts 3-6 were obtained after removal of the diethyl ester using bromot-rimethylsilane, hydrolysis of the resulting silylester with water, and treatment with 1 equivalent of sodium hydroxide.

Scheme 1. Synthesis of O-linked compounds 3-6.$^a$

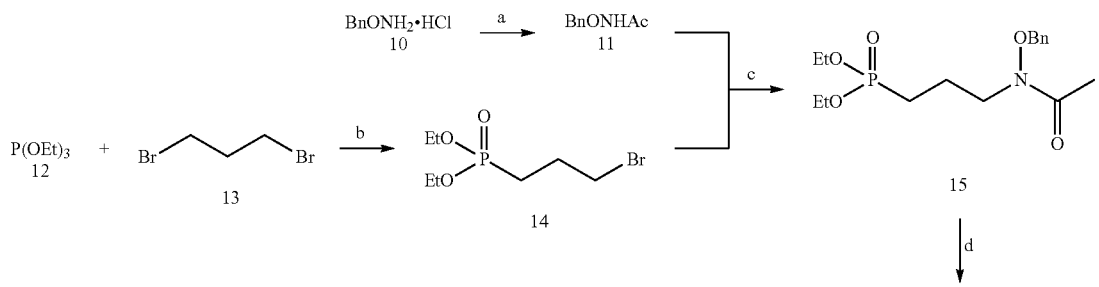

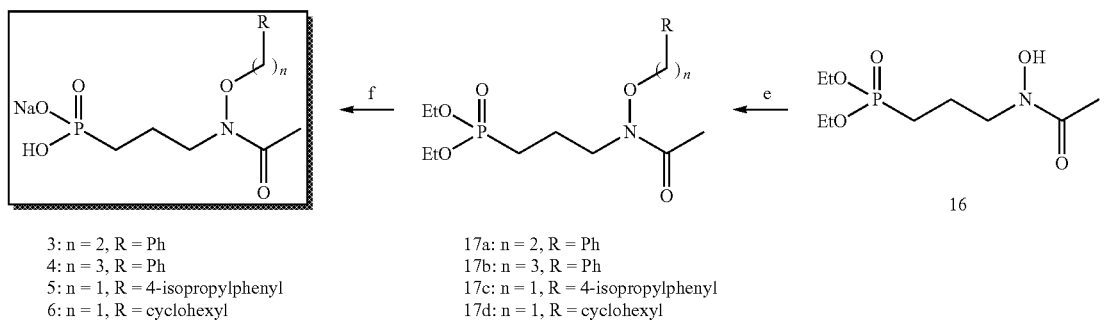

3: n = 2, R = Ph
4: n = 3, R = Ph
5: n = 1, R = 4-isopropylphenyl
6: n = 1, R = cyclohexyl 17a: n = 2, R = Ph
17b: n = 3, R = Ph
17c: n = 1, R = 4-isopropylphenyl
17d: n = 1, R = cyclohexyl

[a]Reagents and conditions: (a) Et$_3$N, AcCl, CH$_2$Cl$_2$; (b) microwave; (c) NaH, NaI, THF, 70° C.; (d) Pd/C, H$_2$, MeOH, (e) NaH, R(CH$_2$)$_n$Br, THF, 70° C.; (f) i: TMSBr, CH$_2$Cl$_2$, ii: H$_2$O, iii: NaOHaq.

The amide ligands 7 and 8 were prepared using the synthesis described in Scheme 2. Aldehyde 19 was synthesized from the commercially available acetal 18 in acidic conditions. Compound 19 was combined with O-benzylhydroxylamine, and then reduction with sodium cyanoborohydride and hydrochloric acid gave diethyl ester 20. Alkylation of 20 using sodium hydride and the corresponding arylalkyl chloride, gave the expected monosodium salts 7 and 8 after deprotection of the hydroxamate and the phosphonate esters.

Scheme 2. Synthesis of amide ligands 7 and 8.[a]

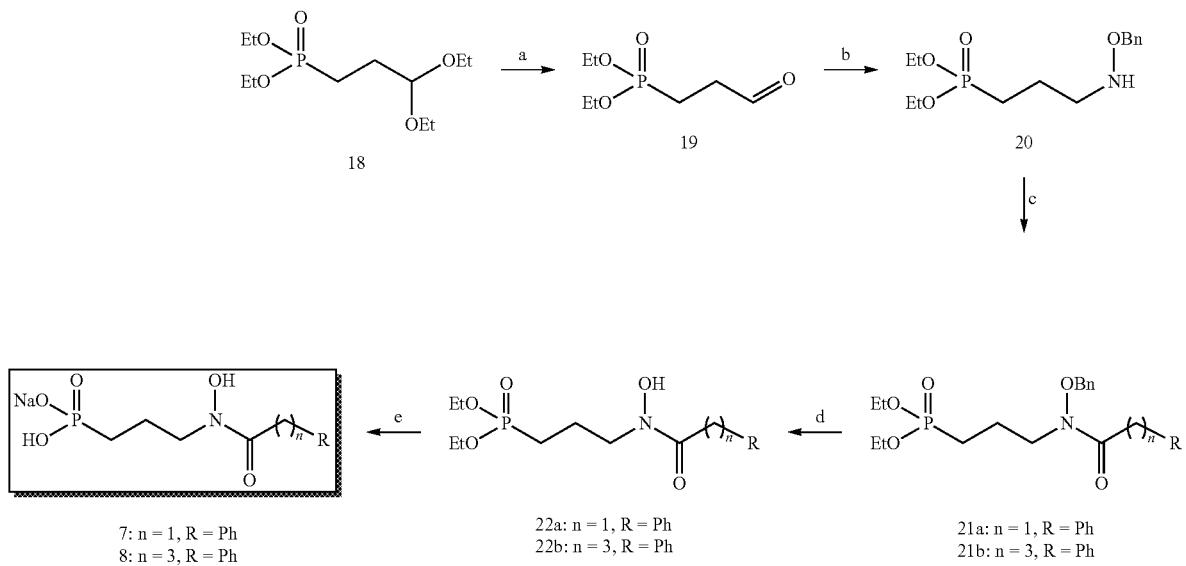

7: n = 1, R = Ph
8: n = 3, R = Ph

22a: n = 1, R = Ph
22b: n = 3, R = Ph

21a: n = 1, R = Ph
21b: n = 3, R = Ph

[a]Reagents and conditions: (a) 2N HCl; (b) BnONH$_2$, MeOH, 40° C., then NaBH$_3$CN, HCl, MeOH; (c) Et$_3$N, R(CH$_2$)$_n$COCl, CH$_2$Cl$_2$; (d) Pd/C, H$_2$, MeOH, (e) i: TMSBr, CH$_2$Cl$_2$, ii: H$_2$O, iii: NaOHaq.

Amide 9 was prepared according the pathway in Scheme 3, with the introduction or the cyclohexyl group at the beginning of the synthesis. Compound 24, obtained by acylation O-benzylhydroxylamine hydrochloride 10 with cyclohexanecarbonyl chloride 23, was treated with 3-bromopropylphosphonate 14 to give diethyl phosphonate 25, which was subsequently debenzylated to afford 26. TMSBr deprotection of the phosphonate diester and basic workup yielded the expected monosodium salt 9.

Scheme 3. Synthesis of the amide ligand 9.[a]

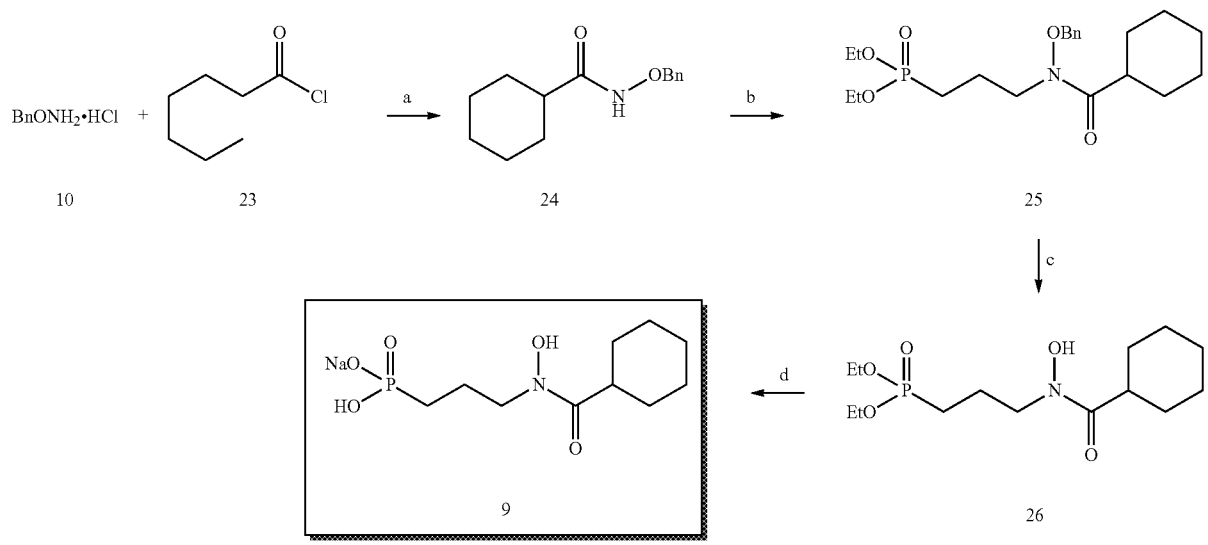

[a]Reagents and conditions: (a) Et$_3$N, CH$_2$Cl$_2$; (b) NaH, 14, THF, 70° C.; (c) Pd/C, H$_2$, MeOH, (d) i: TMSBr, CH$_2$Cl$_2$, ii: H$_2$O, iii: NaOHaq.

As has been seen with related compounds (Zinglé et al. *J. Org. Chem.* 2010, 75, 3203-3207), most of the monosodium salts were isolated and evaluated as a mixture of two conformers. Indeed, Zinglé et al. showed that N-substituted or N- and O-substituted hydroxamic acids were usually present as a mixture of Z and E conformers because of the restricted rotation around the C—N bond (Henriksson et al.). Moreover, the ratio was dependent on the substituent and the nature of the solvent.

Compounds 3-9 were tested for their inhibitory effect against purified *M. tuberculosis* Dxr using the reported spectrophotometric assay following NADPH depletion at 340 nm (Henriksson et al.). IC$_{50}$ values, or percentage of remaining enzyme activity, are shown in Table 5. Fosmidomycin (1) and FR900098 (2) were included for comparison.

Among the ether ligands, all showed inhibition of Dxr with the exception of compound 4. The best in this series was compound 5, having an IC$_{50}$ of 50.6 μM. Interestingly, the amide ligands appear to be generally better inhibitors of the enzyme. Amides 7 and 8 have IC$_{50}$ values of 7.5 and 3.1 μM, respectively, close to that of the parent compound FR900098 (2, IC$_{50}$—2.0 μM). The weaker IC$_{50}$ values of compounds 6 and 9 (197.6 and 57.8 respectively), both substituted with a cyclohexyl substituent, confirmed the importance of the aromatic group in the NADPH pocket. Taken together, the series with better GScores displayed better inhibition of the enzyme, validating our approach toward ligand design.

There is an urgent need for the development of novel, highly active, and less toxic anti-TB drugs. Dxr in the nonmevalonate pathway is an attractive target since humans do not have the enzyme or its homologue. Dxr inhibitors should be effective against drug-resistant Mtb strains, and against both latent and active tuberculosis. Moreover, Dxr is used by other pathogenic organisms such as *Plasmodium falciparum* (responsible for malaria), *Bacillus anthracis* (responsible for anthrax) and *E. coli*, so inhibitors of this enzyme might yield important leads for other therapeutic areas. Importantly, the available crystal structure of Mtb Dxr in complex with NADPH and fosmidomycin facilitated structure-based inhibitor design. The results of our clocking studies suggest that analogs of fosmidomycin and FR900098, amide- or O-substituted on the hydroxamate moiety with an aryl or alkyl group, are promising candidates for the development of novel and potent inhibitors against Mtb Dxr. These compounds are predicted to occupy both the DXP and NADPH binding sites on the enzyme which could result in higher affinity than that of fosmidomycin. The inhibition data from our initial set of ether and amide ligands (3-9) show promising results, with our best compound (8) having an IC$_{50}$ of 3.1 μM. This study opens new perspectives in the design and development of novel Dxr inhibitors.

Example 3

We present a series of analogs of phosmidomycin and FR900098 (compounds 1 and 2, respectively) designed to understand if added lipophilicity increases cell penetration and antibacterial activity. It is expected that these prodrugs enter the cell and are hydrolyzed by nonspecific, cellular esterases to reveal the phosphonate which then inhibits Dxr. The compounds have the general structure shown in the following Chart 2.

Chart 2. Lipophilic esters of phosmidomycin and FR900098. R = , CH3; R1 = various alkyl groups.

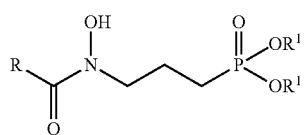

We devised novel synthetic routes to prepare the analogs. The syntheses of the target compounds are shown in Schemes 4-6. Diethyl fosmidomycin (10) was prepared using the route shown in Scheme 1. Diethyl phosphite (3) was combined with O-benzylhydroxylamine (4) to yield phosphoramidate (5). This compound was combined with diethyl 3-bromopropylphosphonate (6) to yield compound 7. The phosphoramide of 7 was cleaved using acidic conditions to yield compound 8. Compound 8 was formylated and debenzylated to give compounds 9 and 10, respectively.

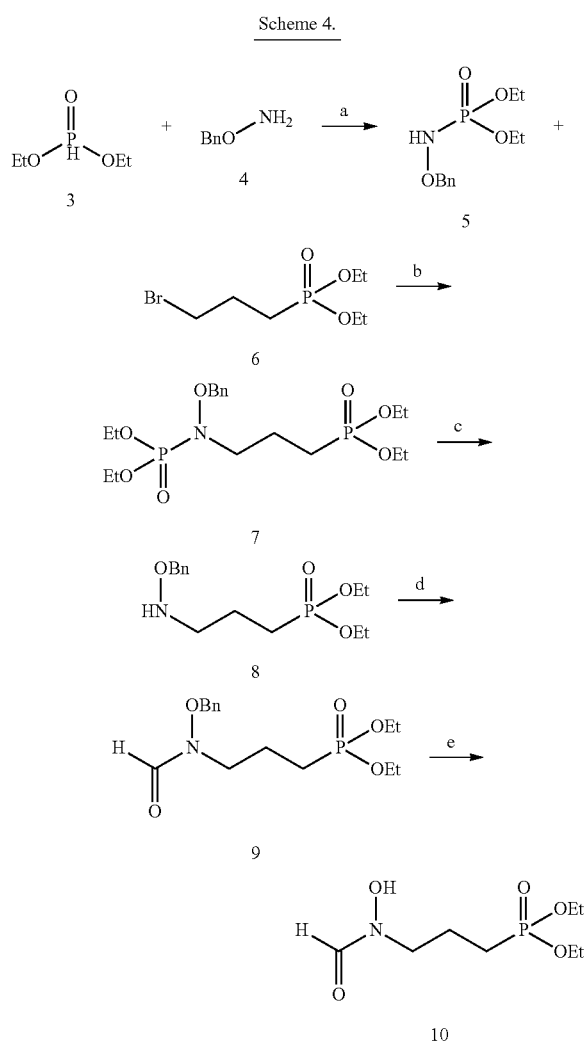

Reagents and conditions: (a) TBABr, CCl$_4$, KHCO$_3$, K$_2$CO$_3$, CH$_2$Cl$_2$; (b) NaH, TBABr, NaI, THF; (c) HCl, EtOH; (d) (CH$_3$CO)$_2$O, HCO$_2$H; (e) H$_2$, 10% Pd/C, MeOH.

Two routes were used in the preparation of lipophilic esters of FR900098 (Schemes 5 and 6). Scheme 5 begins with the lipophilic moieties installed on the phosphonate (compounds 12). To prepare ethyl analog 15, O-benzylhydroxylamine was acetylated and combined with 12a (prepared using microwave conditions (Villemin et al., *Phosphorus, Sulfur Silicon* 1998, 133, 209.) to yield compound 14a.25 For isopropyl analog 16, Boc-protected 11 was alkylated with compound 12b to give 13. Removal of the Boc group followed by acetylation yielded compound 14b. Hydrogenation to remove the benzyl group gave target compounds 15 and 16.

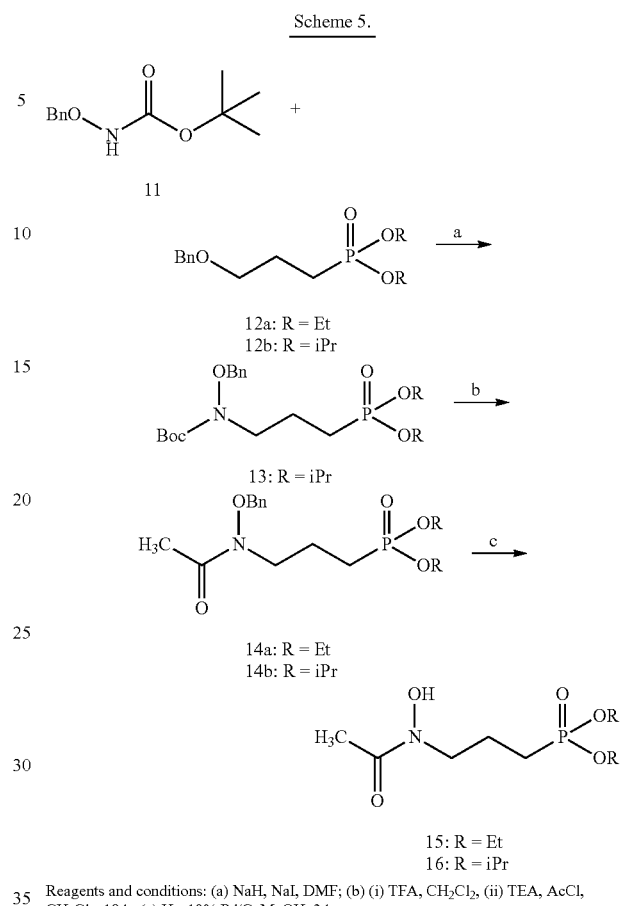

Reagents and conditions: (a) NaH, NaI, DMF; (b) (i) TFA, CH$_2$Cl$_2$, (ii) TEA, AcCl, CH$_2$Cl$_2$, 18 h; (c) H$_2$, 10% Pd/C, MeOH, 2 h.

Most of the lipophilic esters were prepared using the route shown in Scheme 6. This scheme uses a shorter, but more costly, path to compound 8. Diethyl acetal-protected diethyl phosphonate ester 17 was deprotected to give aldehyde 18. This compound underwent reductive amination with O-benzylhydroxylamine and NaBH3CN to yield compound 8. Acetylation yielded compound 14a. Removal of the diethyl ester using TMSBr gave common intermediate 19. Interestingly, despite its use by many groups, the TMSBr deprotection step was not well described. In our hands, the addition of water after deprotection did not yield a solid. The solid, deprotected product was isolated only after complete removal of water or with the addition of THF to facilitate precipitation. Intermediate 19 was alkylated with several alkyl groups to give compounds 20a~g. Subsequent hydrogenation yielded target compounds 21-27. The analytical data for compounds 22, 24, and 27 matches literature values (Ortmann et al. *Arch. Pharm.* (*Weinheim*) 2005, 338, 305). Experimental details are given for new compounds 21, 23, 25, and 26.

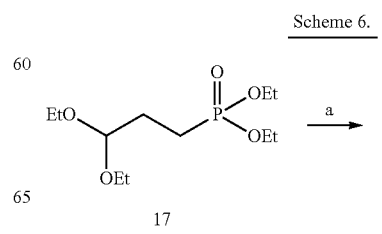

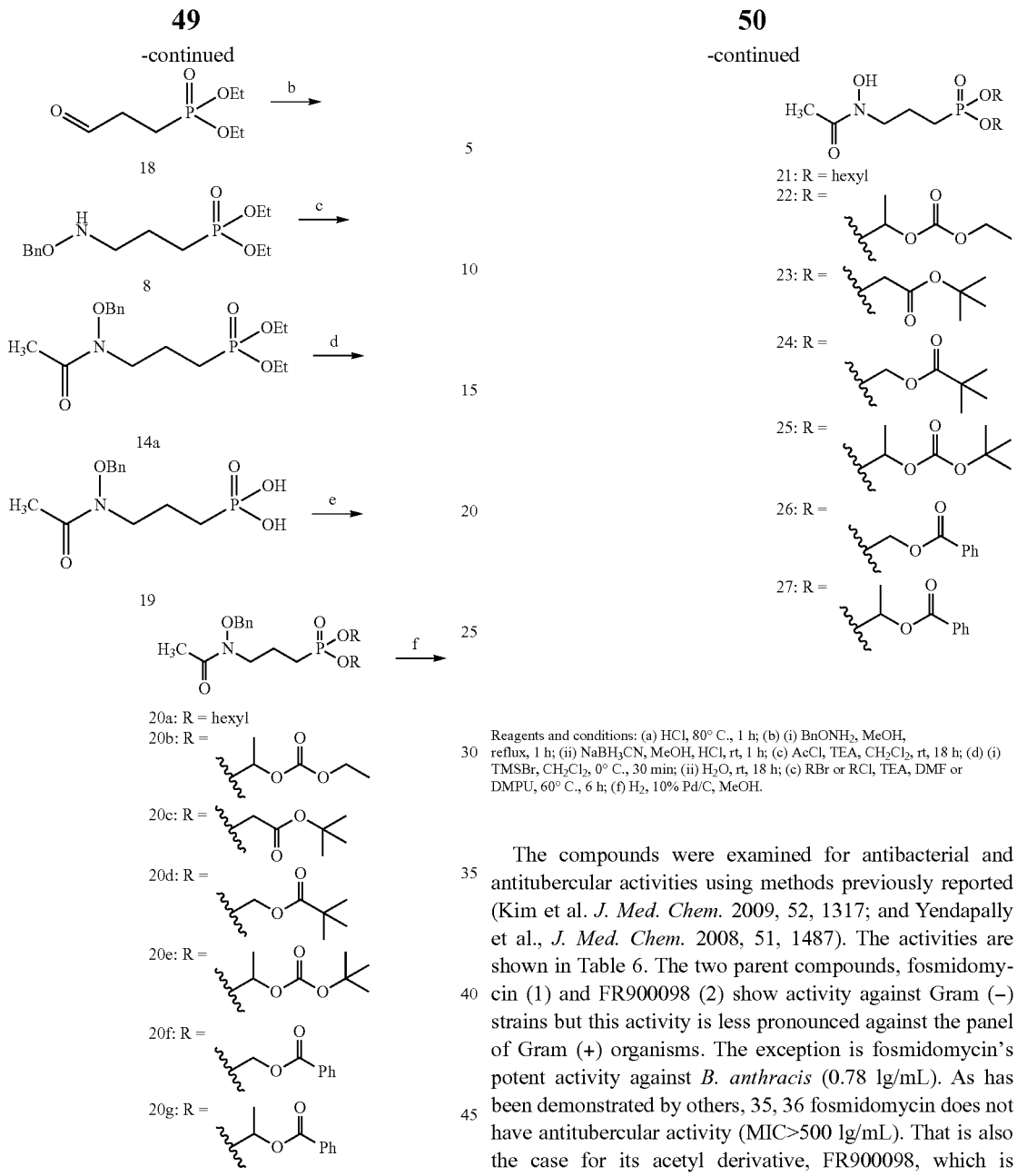

Reagents and conditions: (a) HCl, 80° C., 1 h; (b) (i) BnONH$_2$, MeOH, reflux, 1 h; (ii) NaBH$_3$CN, MeOH, HCl, rt, 1 h; (c) AcCl, TEA, CH$_2$Cl$_2$, rt, 18 h; (d) (i) TMSBr, CH$_2$Cl$_2$, 0° C., 30 min; (ii) H$_2$O, rt, 18 h; (e) RBr or RCl, TEA, DMF or DMPU, 60° C., 6 h; (f) H$_2$, 10% Pd/C, MeOH.

The compounds were examined for antibacterial and antitubercular activities using methods previously reported (Kim et al. *J. Med. Chem.* 2009, 52, 1317; and Yendapally et al., *J. Med. Chem.* 2008, 51, 1487). The activities are shown in Table 6. The two parent compounds, fosmidomycin (1) and FR900098 (2) show activity against Gram (−) strains but this activity is less pronounced against the panel of Gram (+) organisms. The exception is fosmidomycin's potent activity against *B. anthracis* (0.78 lg/mL). As has been demonstrated by others, 35, 36 fosmidomycin does not have antitubercular activity (MIC>500 lg/mL). That is also the case for its acetyl derivative, FR900098, which is inactive.

TABLE 6

Antiviral activities of compounds 1, 2, 10, 15, 16, and 21-27 (MIC in μg/mL)

| | | | Gram (+) | | | | | Gram (−) | | |
|---|---|---|---|---|---|---|---|---|---|---|
| Compound | R | R$^1$ | B. anthracis | E. faecalis | S. aureus (MSSA) | S. aureus (MRSA) | M. tuberculosis (H37Rv) | Acineto-bacter | E. coli k12 | E. coli tolc |
| Fosmidomycin (1) | H | H/Na[b] | 0.78 | >200 | >200 | 200 | >500 | 100 | 12.5 | 6.25 |
| FR900098 (2) | CH$_3$ | H/Na[b] | 50 | >200 | >200 | 50 | >500 | 50 | 200 | 12.5 |
| 10 | H | Et | >200 | >200 | >200 | >200 | 400 | >200 | >200 | >200 |
| 15 | CH$_3$ | Et | 200 | >200 | >200 | 200 | 200-400 | >200 | >200 | >200 |

TABLE 6-continued

Antiviral activities of compounds 1, 2, 10, 15, 16, and 21-27 (MIC in μg/mL)

$$R-\overset{\displaystyle O}{\underset{\displaystyle \|}{C}}-\overset{\displaystyle OH}{\underset{\displaystyle |}{N}}-CH_2CH_2CH_2-\overset{\displaystyle O}{\underset{\displaystyle \|}{P}}(OR^1)_2$$

| | | | Gram (+) | | | | | Gram (−) | | |
|---|---|---|---|---|---|---|---|---|---|---|
| Compound | R | R$^1$ | B. anthracis | E. faecalis | S. aureus (MSSA) | S. aureus (MRSA) | M. tuberculosis (H37Rv) | Acineto-bacter | E. coli k12 | E. coli tolc |
| 16 | CH$_3$ | iPr | >200 | >200 | >200 | >200 | 400 | >200 | >200 | >200 |
| 21 | CH$_3$ | n-hexyl | ND$^c$ | ND | ND | ND | 100 | ND | ND | ND |
| 22 | CH$_3$ | CH(CH$_3$)OC(O)OEt | >200 | >200 | >200 | >200 | 400 | >200 | >200 | 200 |
| 23 | CH$_3$ | CH$_2$C(O)OtBu | >200 | >200 | 100 | 25 | 400 | >200 | >200 | >200 |
| 24 | CH$_3$ | CH$_2$OC(O)tBu | 200 | >200 | 100 | 50 | 50-100 | >200 | >200 | 100 |
| 25 | CH$_3$ | CH(CH$_3$)OC(O)OtBu | 200 | >200 | 100 | 50 | 400 | >200 | >200 | >200 |
| 26 | CH$_3$ | CH$_2$OC(O)Ph | 100 | >200 | >200 | >200 | 25-100 | 200 | >200 | 50 |
| 27 | CH$_3$ | CH(CH$_3$)OC(O)Ph | 50 | >200 | >200 | >200 | 100-200 | 100 | 50 | 50 |

$^b$Compounds 1 and 2 used as monosodium salts.
$^c$ND-not determined

Several of the lipophilic esters showed improved activity relative to fosmidomycin, particularly for Gram (+) bacteria. While diethyl fosmidomycin (10) showed little activity against the panel, as the size of the lipophilic ester increased, activity against these organisms generally increased as well. For example, 24 and 26 showed better antitubercular activity compared with compounds 10, 15 and 16. Interestingly, analogs with a secondary ester (22, 25 and 27) did not outperform their primary counterparts. A possible explanation for this could be that the cellular esterases needed to reveal the phosphonate do not tolerate branching within the ester. Lack of activity of this family of esters in certain strains may be due to efflux mechanisms or inefficient cleavage of the ester.

Our results suggest that lipophilic esters of fosmidomycin and FR900098 improve cell activity and antibacterial activity for certain organisms. While fosmidomycin takes advantage of GlpT for cell entry, these lipophilic esters are not reliant on this transporter. As glpT mutation is the only documented path toward fosmidomycin resistance, we expect these compounds to avoid such a resistance pathway. Dxr inhibitors optimized for both cell penetration and the enzyme's active site could provide an important tool for target validation on the road toward development of a novel therapeutic.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A compound having the chemical structure of formula (II)

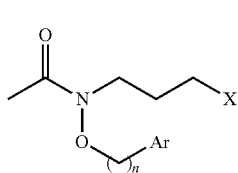

wherein X is 1) a carboxylate, phosphonate, sulfate, an ester thereof, or a salt thereof, or 2) a tetrazole; Ar is a substituted or unsubstituted aromatic or heteroaromatic group; and n is 0, 1, 2, 3, or 4, wherein "n is 1" and

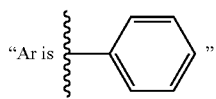

are not simultaneously satisfied.

2. The compound of claim 1, wherein Ar is a phenyl or a heteroaromatic group.

3. A compound having the chemical structure of formula (II)

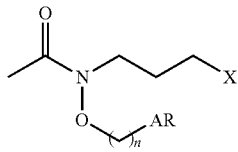

wherein X is 1) a carboxylate, phosphonate, sulfate, an ester thereof, or a salt thereof, or 2) a tetrazol; Ar is a substituted or unsubstituted aromatic or heteroaromatic group; and wherein n is 2, 3, or 4.

4. A compound having the chemical structure of formula (II)

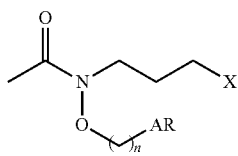

wherein X is a phosphonate, an ester thereof, or a salt thereof; Ar is a substituted or unsubstituted aromatic or heteroaromatic group; and n is 0, 1, 2, 3, or 4, wherein "n is 1" and

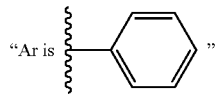

are not simultaneously satisfied.

5. The compound of claim 1, selected from the group consisting of:

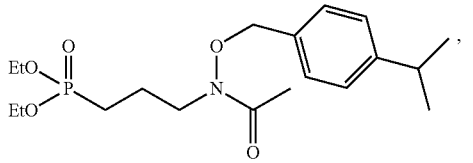

-continued

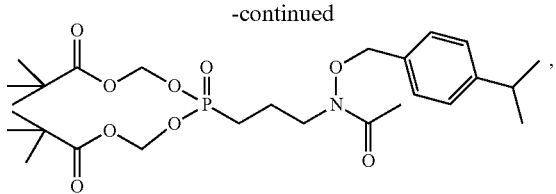

and

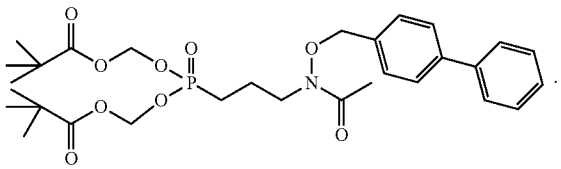

6. A pharmaceutical composition comprising a compound having the chemical structure of formula (II)

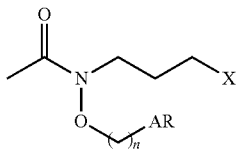
(II)

wherein X is 1) a carboxylate, phosphonate, sulfate, an ester thereof, or a salt thereof, or 2) tetrazole; Ar is a substituted or unsubstituted aromatic or heteroaromatic group; and n is 0, 1, 2, 3, or 4, wherein "n is 1" and

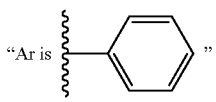 [SMILES: *c1ccccc1]

are not simultaneously satisfied.

7. The composition of claim 6, wherein Ar is a phenyl or a heteroaromatic group.

8. A pharmaceutical composition comprising a compound having the chemical structure of formula (II)

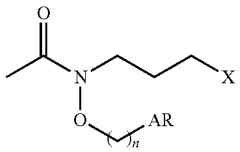
(II)

where X is 1) a carboxylate, phosphonate, sulfate, an ester thereof, or a salt thereof, or 2) a tetrazole; Ar is a substituted or unsubstituted aromatic or heteroaromatic group; wherein n is 2, 3, or 4.

9. A pharmaceutical composition comprising the compound of claim 5.

* * * * *